(12) United States Patent
Murakami

(10) Patent No.: US 11,957,518 B2
(45) Date of Patent: Apr. 16, 2024

(54) ULTRASOUND SYSTEM AND CONTROL METHOD OF ULTRASOUND SYSTEM

(71) Applicant: FUJIFILM Corporation, Tokyo (JP)

(72) Inventor: Hiroshi Murakami, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 243 days.

(21) Appl. No.: 17/584,999

(22) Filed: Jan. 26, 2022

(65) Prior Publication Data

US 2022/0142616 A1 May 12, 2022

Related U.S. Application Data

(63) Continuation of application No. PCT/JP2020/026748, filed on Jul. 8, 2020.

(30) Foreign Application Priority Data

Sep. 13, 2019 (JP) .................................. 2019-167544

(51) Int. Cl.
*A61B 8/00* (2006.01)
*A61B 8/14* (2006.01)

(52) U.S. Cl.
CPC .................. *A61B 8/54* (2013.01); *A61B 8/14* (2013.01); *A61B 8/4472* (2013.01); *A61B 8/4488* (2013.01); *A61B 8/463* (2013.01); *A61B 8/469* (2013.01)

(58) Field of Classification Search
CPC .............. A61B 8/54; A61B 8/56; A61B 8/565
See application file for complete search history.

(56) References Cited

U.S. PATENT DOCUMENTS

| | | |
|---|---|---|
| 2015/0320439 A1 | 11/2015 | Andrews et al. |
| 2017/0086798 A1 | 3/2017 | Bjaerum et al. |
| 2018/0116636 A1 | 5/2018 | Yoneda et al. |
| 2019/0069884 A1 | 3/2019 | Dickie et al. |

FOREIGN PATENT DOCUMENTS

| | | |
|---|---|---|
| JP | 2006-95071 A | 4/2006 |
| JP | 2007-282957 A | 11/2007 |
| JP | 2015-521885 A | 8/2015 |
| JP | 2015-211726 A | 11/2015 |
| JP | 2017-18276 A | 1/2017 |
| JP | 2017-99785 A | 6/2017 |

OTHER PUBLICATIONS

International Search Report issued in PCT/JP2020/026748; dated Aug. 11, 2020.
Written Opinion issued in PCT/JP2020/026748; dated Aug. 11, 2020.
Extended European Search Report issued in EP 20 862 030.2 by the European Patent Office dated Sep. 15, 2022.

*Primary Examiner* — Colin T. Sakamoto
(74) *Attorney, Agent, or Firm* — Studebaker & Brackett PC

(57) ABSTRACT

A probe-side processor generates image information data on the basis of a sound ray signal generated, and the image information data generated by the probe-side processor is stored in a probe-side cine-memory. In a case where a freeze mode is designated, the past image information data stored in the probe-side cine-memory is wirelessly transmitted from the probe-side wireless communication circuit, and a terminal-side processor displays an ultrasound image on a monitor on the basis of the past image information data received by a terminal-side wireless communication circuit.

23 Claims, 11 Drawing Sheets

ULTRASOUND SYSTEM AND CONTROL METHOD OF ULTRASOUND SYSTEM

CROSS-REFERENCE TO RELATED APPLICATIONS

This application is a Continuation of PCT International Application No. PCT/JP2020/026748 filed on Jul. 8, 2020, which claims priority under 35 U.S.C. § 119(a) to Japanese Patent Application No. 2019-167544 filed on Sep. 13, 2019. Each of the above applications is hereby expressly incorporated by reference, in its entirety, into the present application.

BACKGROUND OF THE INVENTION

1. Field of the Invention

The present invention relates to an ultrasound system in which an ultrasound probe and an information terminal are wirelessly connected, and a control method of the ultrasound system.

2. Description of the Related Art

In the related art, in the medical field, an ultrasound system using an ultrasound image has been put to practical use. In general, this type of ultrasound system comprises an ultrasound probe with a built-in transducer array, and an information terminal connected to the ultrasound probe, and the ultrasound system causes the ultrasound probe to transmit an ultrasound beam toward a subject, receives an ultrasound echo from the subject by the ultrasound probe, and electrically processes a reception signal thereof in the information terminal to generate an ultrasound image.

Further, in recent years, an ultrasound system has been developed which is intended to improve operability and mobility of an ultrasound probe by wirelessly connecting the ultrasound probe and an information terminal by wireless communication, as disclosed in JP2015-211726A.

In such a wireless connection type ultrasound system, the analog reception signal output from the transducer array of the ultrasound probe is transmitted to the information terminal by wireless communication, or a circuit for signal processing is built in the ultrasound probe and the reception signal output from the transducer array is subjected to digital processing in the ultrasound probe and transmitted to the information terminal by wireless communication, and thereby an ultrasound image is generated in the information terminal.

In the ultrasound system in the related art which performs wireless communication, as disclosed in JP2006-95071A and JP2015-521885A, a cine-memory for storing ultrasound images of past frames is included in the information terminal side. In a case of a live mode, for the ultrasound image of each frame wirelessly transmitted from the ultrasound probe to the information terminal, ultrasound images of the number of frames corresponding to the memory capacity from the ultrasound image of the latest frame are stored in the cine-memory, and in a case of a freeze mode, the ultrasound image of the past frame stored in the cine-memory is read and displayed on a monitor.

SUMMARY OF THE INVENTION

However, in the ultrasound system in the related art which performs wireless communication, due to fluctuations in the wireless communication band, in the case of the live mode, ultrasound images of all frames wirelessly transmitted from the ultrasound probe cannot be wirelessly transmitted in real time, and the ultrasound images of which at least a part of the frames are omitted are stored in the cine-memory of the information terminal in some cases. Thus, in the case of the freeze mode, the ultrasound images of the omitted frames cannot be displayed, and there is a problem that it is not possible to display the ultrasound image that is continuously and correctly changed along the time axis.

Thus, an object of the present invention is to provide an ultrasound system and a control method of the ultrasound system, which resolve the problem in the related art and can display the ultrasound image that is continuously and correctly changed along the time axis in the case of the freeze mode.

In order to achieve the object, the present invention provides an ultrasound system in which an ultrasound probe and an information terminal are wirelessly connected, in which the ultrasound probe includes a transducer array, a transmission and reception circuit that causes the transducer array to transmit an ultrasonic wave, and performs reception focusing processing on a reception signal output from the transducer array that has received an ultrasound echo to generate a sound ray signal, an image information data generation unit that generates image information data on the basis of the sound ray signal generated by the transmission and reception circuit, a probe-side cine-memory that stores the image information data generated by the image information data generation unit, and a probe-side wireless communication circuit that wirelessly transmits the image information data generated by the image information data generation unit, the information terminal includes a monitor, an input device, a terminal-side wireless communication circuit that receives the image information data wirelessly transmitted from the probe-side wireless communication circuit, and a display control unit that displays an ultrasound image on the monitor on the basis of the image information data received by the terminal-side wireless communication circuit, and in a case where a freeze mode is designated on the basis of an instruction input from the input device and transmission of the ultrasonic wave from the transducer array is stopped, the image information data of past frames stored in the probe-side cine-memory is wirelessly transmitted from the probe-side wireless communication circuit, and the display control unit displays the ultrasound image on the monitor on the basis of the image information data of the past frames received by the terminal-side wireless communication circuit.

Here, it is preferable that the ultrasound probe further includes a frame adjustment unit that adjusts whether to output the image information data of all the frames generated by the image information data generation unit or to output the image information data generated by the image information data generation unit by omitting the image information data of at least a part of the frames, according to fluctuations in a wireless transmission band by the probe-side wireless communication circuit, and in a case where a live mode is designated on the basis of the instruction input from the input device and transmission of the ultrasonic wave from the transducer array is started, the image information data adjusted by the frame adjustment unit is wirelessly transmitted from the probe-side wireless communication circuit, and the display control unit displays the ultrasound image on the monitor on the basis of the image information data received by the terminal-side wireless communication circuit.

It is preferable that the information terminal further includes a terminal-side cine-memory that stores the image information data received by the terminal-side wireless communication circuit, in the case of the live mode, the image information data adjusted by the frame adjustment unit is wirelessly transmitted from the probe-side wireless communication circuit, and the image information data received by the terminal-side wireless communication circuit is stored in the terminal-side cine-memory, and in the case of the freeze mode, the image information data of the at least a part of frames omitted by the frame adjustment unit is read from the probe-side cine-memory, and is wirelessly transmitted from the probe-side wireless communication circuit, the image information data of the at least a part of frames received by the terminal-side wireless communication circuit is stored in the terminal-side cine-memory, and the display control unit displays the ultrasound image on the monitor on the basis of the image information data stored in the terminal-side cine-memory.

It is preferable that, immediately after the freeze mode is designated, the image information data of the at least a part of frames omitted by the frame adjustment unit is wirelessly transmitted from the probe-side wireless communication circuit.

It is preferable that, on the basis of the instruction input from the input device, the ultrasound image of a frame in the vicinity of the at least a part of frames of the image information data omitted by the frame adjustment unit is designated from the image information data stored in the terminal-side cine-memory, and immediately after the ultrasound image is displayed on the monitor on the basis of the designated image information data of the frame in the vicinity of the omitted at least a part of frames, the image information data of the at least a part of frames omitted by the frame adjustment unit is wirelessly transmitted from the probe-side wireless communication circuit.

Further, it is preferable that in the case of the freeze mode, the at least a part of frames of the image information data omitted by the frame adjustment unit is detected from the image information data stored in the terminal-side cine-memory, and the image information data of the at least a part of frames omitted by the frame adjustment unit is wirelessly transmitted from the probe-side wireless communication circuit on the basis of the detected at least a part of frames of the image information data.

It is preferable that in the case of the live mode, the frame adjustment unit generates an omitted frame list for managing the at least a part of frames of the image information data omitted from the image information data wirelessly transmitted by the probe-side wireless communication circuit, and in the case of the freeze mode, the image information data of the at least a part of frames omitted by the frame adjustment unit is wirelessly transmitted from the probe-side wireless communication circuit on the basis of the omitted frame list generated by the frame adjustment unit.

It is preferable that detection of the at least a part of frames of the image information data omitted by the frame adjustment unit is sequentially performed for the frame of the image information data pointed to by a scan pointer, from the frame of the image information data corresponding to the ultrasound image being displayed on the monitor toward the past frame of the image information data among the image information data stored in the terminal-side cine-memory.

It is preferable that in a case where the frame of the image information data pointed to by the scan pointer is moved to the past frame of the image information data earlier than the frame of the ultrasound image being displayed on the monitor on the basis of the instruction input from the input device, the frame of the image information data pointed to by the scan pointer is changed to the moved past frame of the image information data, and the detection of the at least a part of frames of the image information data omitted by the frame adjustment unit is sequentially performed for the frame of the image information data pointed to by the scan pointer, from the changed past frame of the image information data pointed to by the scan pointer toward the latest frame of the image information data, and in a case where the frame of the image information data pointed to by the scan pointer reaches the latest frame of the image information data, the frame of the image information data pointed to by the scan pointer is changed to the moved past frame of the image information data, and the detection of the at least a part of frames of the image information data omitted by the frame adjustment unit is sequentially performed for the frame of the image information data pointed to by the scan pointer, from the changed past frame of the image information data pointed to by the scan pointer toward the past frame of the image information data which is further earlier than the changed past frame of the image information data.

It is preferable that the number of frames of the image information data to be stored in the probe-side cine-memory and the number of frames of the image information data to be stored in the terminal-side cine-memory are matched by deciding the number of frames of the image information data to be stored in one of the probe-side cine-memory and the terminal-side cine-memory, which has a larger memory capacity, in accordance with one of the probe-side cine-memory and the terminal-side cine-memory, which has a smaller memory capacity.

It is preferable that in the case of the live mode, the image information data of all the frames generated by the image information data generation unit is stored in the probe-side cine-memory, and in the case of the freeze mode, the image information data of the frame wirelessly transmitted from the probe-side wireless communication circuit and the image information data of the frame for which reception confirmation is notified from the information terminal are deleted from the probe-side cine-memory.

It is preferable that in the case of the live mode, only the image information data of the at least a part of frames omitted by the frame adjustment unit is stored in the probe-side cine-memory, and in the case of the freeze mode, the image information data of the frame for which reception confirmation is notified from the information terminal is deleted from the probe-side cine-memory.

It is preferable that the ultrasound probe further includes an error generation unit that issues an error when the probe-side cine-memory becomes full in the case of the live mode.

It is preferable that in the case of the live mode, the image information data of the frame deleted from the terminal-side cine-memory is deleted from the probe-side cine-memory.

It is preferable that the probe-side cine-memory generates a free space management list for managing a free space of the probe-side cine-memory in the case of the freeze mode, in the case of the freeze mode, a frame region of the probe-side cine-memory where the image information data of the frame deleted from the probe-side cine-memory is stored is the free space in the free space management list, and in the case of the live mode, the image information data of each frame generated by the image information data generation unit is sequentially stored from the frame region of the probe-side cine-memory corresponding to a head free space of the free space management list.

It is preferable that the image information data generation unit includes a signal processing unit that generates image signal data before imaging into the ultrasound image on the basis of the sound ray signal generated by the transmission and reception circuit, and an image processing unit that generates the ultrasound image as the image information data generated by the image information data generation unit on the basis of the image signal data generated by the signal processing unit, and the display control unit displays the ultrasound image received by the terminal-side wireless communication circuit on the monitor.

It is preferable that the image information data generation unit includes a signal processing unit that generates image signal data before imaging into the ultrasound image as the image information data generated by the image information data generation unit, on the basis of the sound ray signal generated by the transmission and reception circuit, the information terminal includes an image processing unit that generates the ultrasound image on the basis of the image signal data received by the terminal-side wireless communication circuit, and the display control unit displays the ultrasound image generated by the image processing unit on the monitor.

It is preferable that the terminal-side cine-memory stores the ultrasound image generated by the image processing unit.

The present invention provides a control method of an ultrasound system in which an ultrasound probe and an information terminal are wirelessly connected, and the control method comprises a step of causing a transducer array to transmit an ultrasonic wave, and performing reception focusing processing on a reception signal output from the transducer array that has received an ultrasound echo to generate a sound ray signal, by a transmission and reception circuit of the ultrasound probe; a step of generating image information data on the basis of the generated sound ray signal, by an image information data generation unit of the ultrasound probe; a step of storing the generated image information data, by a probe-side cine-memory of the ultrasound probe; a step of wirelessly transmitting the generated image information data, by a probe-side wireless communication circuit of the ultrasound probe; a step of receiving the wirelessly transmitted image information data, by a terminal-side wireless communication circuit of the information terminal; and a step of displaying an ultrasound image on the monitor on the basis of the received image information data, by a display control unit of the information terminal, in which in a case where a freeze mode is designated on the basis of an instruction input from an input device and transmission of the ultrasonic wave from the transducer array is stopped, the image information data of past frames stored in the probe-side cine-memory is wirelessly transmitted from the probe-side wireless communication circuit, and the display control unit displays the ultrasound image on the monitor on the basis of the image information data of the past frames received by the terminal-side wireless communication circuit.

Here, it is preferable that the control method further comprises a step of adjusting whether to output the image information data of all the frames generated by the image information data generation unit or to output the image information data generated by the image information data generation unit by omitting the image information data of at least a part of the frames, according to fluctuations in a wireless transmission band by the probe-side wireless communication circuit, by a frame adjustment unit of the ultrasound probe, in which in a case where a live mode is designated on the basis of the instruction input from the input device and transmission of the ultrasonic wave from the transducer array is started, the image information data adjusted by the frame adjustment unit is wirelessly transmitted from the probe-side wireless communication circuit, and the display control unit displays the ultrasound image on the monitor on the basis of the image information data received by the terminal-side wireless communication circuit.

It is preferable that the control method further comprises a step of storing the image information data received by the terminal-side wireless communication circuit, by a terminal-side cine-memory of the information terminal, in which in the case of the live mode, the image information data adjusted by the frame adjustment unit is wirelessly transmitted from the probe-side wireless communication circuit, and the image information data received by the terminal-side wireless communication circuit is stored in the terminal-side cine-memory, and in the case of the freeze mode, the image information data of the at least a part of frames omitted by the frame adjustment unit is read from the probe-side cine-memory, and is wirelessly transmitted from the probe-side wireless communication circuit, the image information data of the at least a part of frames received by the terminal-side wireless communication circuit is stored in the terminal-side cine-memory, and the display control unit displays the ultrasound image on the monitor on the basis of the image information data stored in the terminal-side cine-memory.

It is preferable that in the case of the live mode, the image information data of all the frames generated by the image information data generation unit is stored in the probe-side cine-memory, and in the case of the freeze mode, the image information data of the frame wirelessly transmitted from the probe-side wireless communication circuit and the image information data of the frame for which reception confirmation is notified from the information terminal are deleted from the probe-side cine-memory.

It is preferable that in the case of the live mode, only the image information data of the at least a part of frames omitted by the frame adjustment unit is stored in the probe-side cine-memory, and in the case of the freeze mode, the image information data of the frame for which reception confirmation is notified from the information terminal is deleted from the probe-side cine-memory.

Further, it is preferable that the transmission and reception circuit, the image information data generation unit, the signal processing unit, the image processing unit, the frame adjustment unit, the error generation unit, the display control unit, and the input device are hardware or a processor that executes a program, and it is preferable that the probe-side cine-memory and the terminal-side cine-memory are hardware or a memory.

In the present invention, in the case of the live mode, the image information data of the past frames for the number of frames corresponding to the memory capacity, from the time point when the freeze mode is designated is stored in the probe-side cine-memory. Therefore, in the case of the freeze mode, the ultrasound images based on the image information data of any frames stored in the probe-side cine-memory can be displayed on the monitor without being omitted, and the ultrasound images that are continuously and correctly changed along the time axis can be displayed on the monitor.

In the present invention, in the case of the freeze mode, the image information data of the omitted frame is wirelessly transmitted from the probe-side cine-memory and is stored in the terminal-side cine-memory. Therefore, for example, even in a case where the ultrasound image of one frame is sequentially displayed frame by frame toward the ultrasound image of the past or latest frame, smooth frame advance can be achieved without the delay due to the wireless transmission, and it is possible to significantly improve the operability for the user.

Further, by deleting the image information data of the frame that is no longer needed from the probe-side cine-memory, it is possible to significantly reduce the memory capacity of the probe-side cine-memory required in the case of the freeze mode, and it is possible to significantly improve the utilization efficiency of the probe-side cine-memory.

DESCRIPTION OF THE PREFERRED EMBODIMENTS

Hereinafter, an ultrasound system and a control method of the ultrasound system according to the present invention will be described in detail on the basis of preferred embodiments illustrated in the accompanying drawings.

Figure 1:
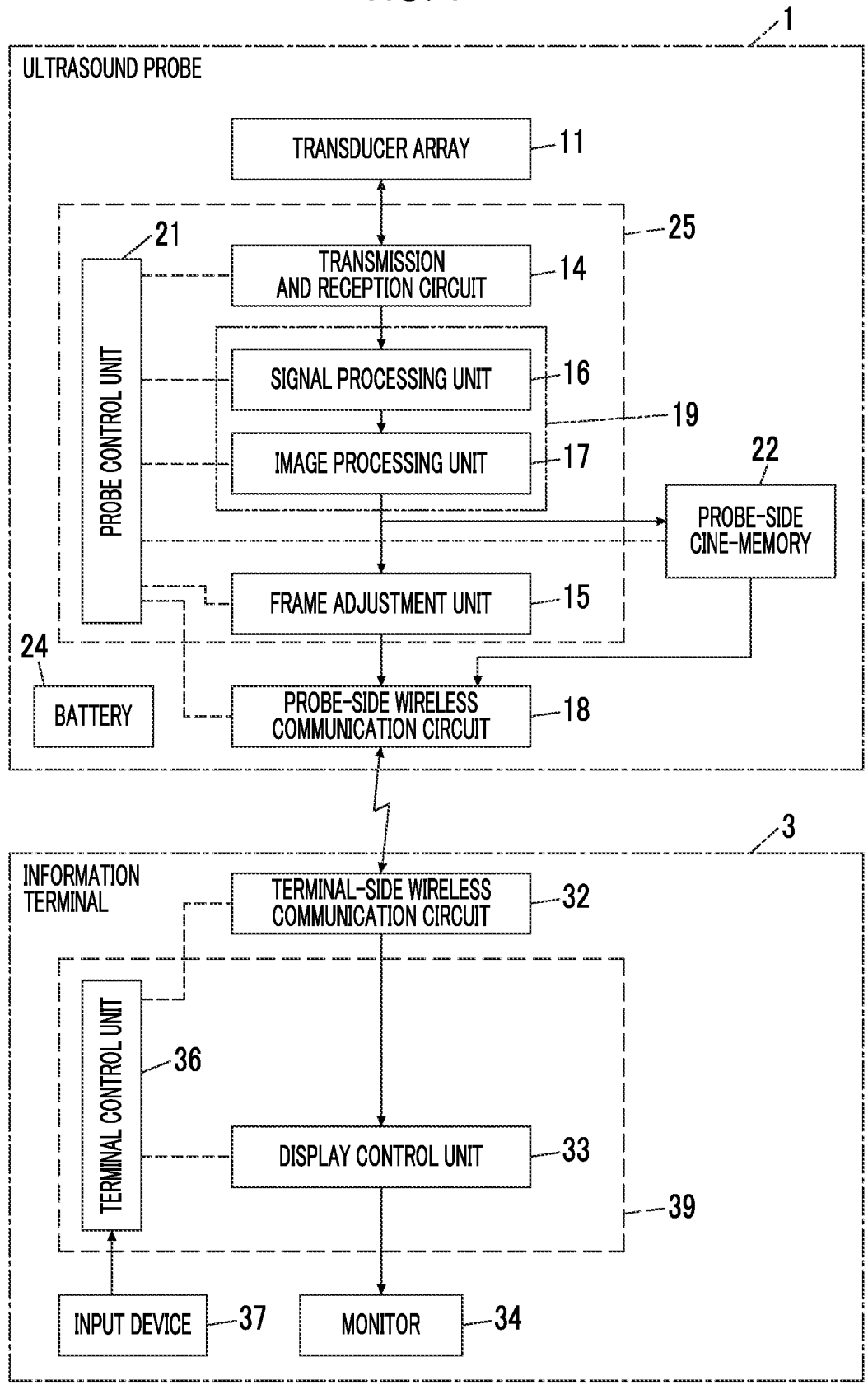
FIG. 1 is a block diagram illustrating a configuration of an ultrasound system of a first embodiment according to the present invention.

FIG. 1 illustrates a block diagram illustrating a configuration of an ultrasound system of a first embodiment according to the present invention. The ultrasound system illustrated in FIG. 1 comprises an ultrasound probe 1 and an information terminal 3, and the ultrasound probe 1 and the information terminal 3 are wirelessly connected by wireless communication.

The ultrasound probe 1 comprises a transducer array 11, and a transmission and reception circuit 14 is bidirectionally connected to the transducer array 11. A signal processing unit 16, an image processing unit 17, a frame adjustment unit 15, and a probe-side wireless communication circuit 18 are sequentially connected in series to the transmission and reception circuit 14. The signal processing unit 16 and the image processing unit 17 constitute an image information data generation unit 19. A probe-side cine-memory 22 is connected to the image processing unit 17, and the probe-side wireless communication circuit 18 is connected to the probe-side cine-memory 22.

Further, a probe control unit 21 is connected to the transmission and reception circuit 14, the signal processing unit 16, the image processing unit 17, the frame adjustment unit 15, the probe-side cine-memory 22, and the probe-side wireless communication circuit 18. A battery 24 is built in the ultrasound probe 1.

The transmission and reception circuit 14, the image information data generation unit 19 (the signal processing unit 16 and the image processing unit 17), the frame adjustment unit 15, and the probe control unit 21 constitute a probe-side processor 25.

The transducer array 11 has a plurality of ultrasonic transducers arranged in a one-dimensional or two-dimensional manner. According to a drive signal supplied from the transmission and reception circuit 14, each of the transducers transmits an ultrasonic wave and receives a reflected wave from the subject to output an analog reception signal.

For example, each transducer is formed by using an element in which electrodes are formed at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

Figure 2:
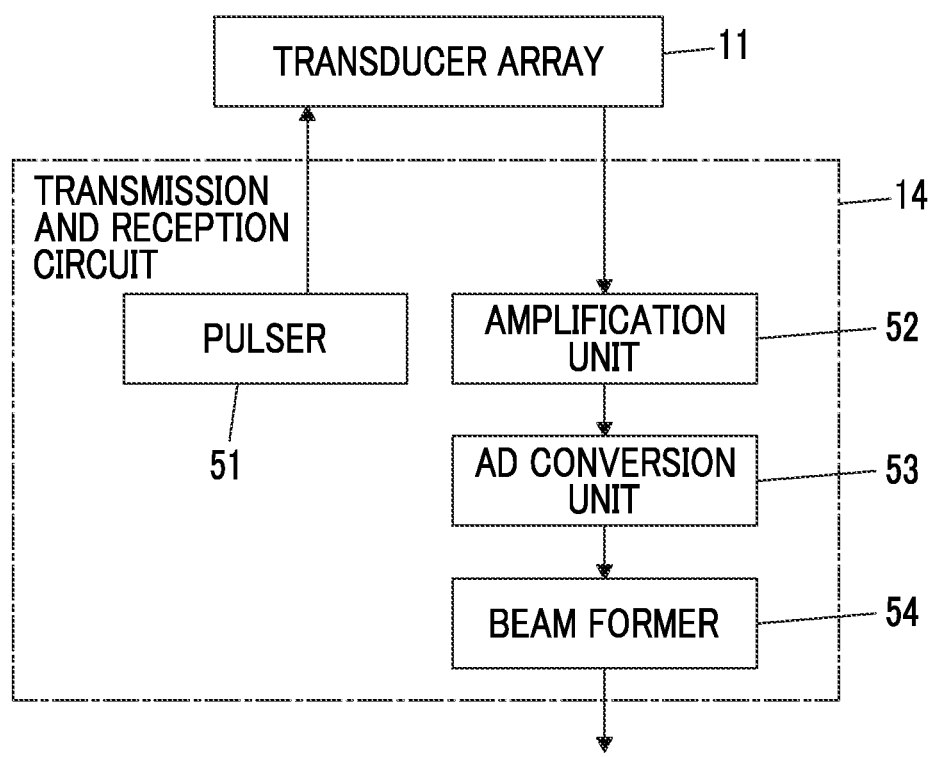
FIG. 2 is a block diagram illustrating a configuration of a transmission and reception circuit illustrated in FIG. 1.

The transmission and reception circuit 14 causes the transducer array 11 to transmit the ultrasonic wave, and performs reception focusing processing on the reception signal output from the transducer array 11 that has received the ultrasound echo to generate a sound ray signal, under the control of the probe control unit 21. As illustrated in FIG. 2, the transmission and reception circuit 14 has a pulser 51 connected to the transducer array 11, and an amplification unit 52, an analog digital (AD) conversion unit 53, and a beam former 54 that are sequentially connected in series from the transducer array 11.

The pulser 51 includes, for example, a plurality of pulse generators, and the pulser 51 adjusts the amount of delay of each drive signal so that ultrasonic waves transmitted from the plurality of transducers of the transducer array 11 form an ultrasound beam on the basis of a transmission delay pattern selected by the probe control unit 21, and supplies the obtained signals to the plurality of transducers. Thus, in a case where a pulsed or continuous-wave voltage is applied to the electrodes of the transducers of the transducer array 11, the piezoelectric body expands and contracts to generate pulsed or continuous-wave ultrasonic waves from each transducer. From the combined wave of these ultrasonic waves, an ultrasound beam is formed.

The transmitted ultrasound beam is reflected by a target, for example, a site of the subject, and propagates toward the transducer array 11 of the ultrasound probe 1. Each transducer constituting the transducer array 11 expands and contracts by receiving the ultrasound echo propagating toward the transducer array 11 in this manner, to generate the reception signal that is an electric signal, and outputs the reception signal to the amplification unit 52.

The amplification unit 52 amplifies the signals input from each transducer constituting the transducer array 11, and transmits the amplified signals to the AD conversion unit 53. The AD conversion unit 53 converts the signal transmitted from the amplification unit 52 into digital reception data, and outputs the reception data to the beam former 54.

The beam former 54 performs so-called reception focusing processing in which addition is performed by giving delays to respective pieces of the reception data converted by the AD conversion unit 53 according to a sound speed distribution or a sound speed set on the basis of a reception delay pattern selected by the probe control unit 21. Through the reception focusing processing, a sound ray signal in which each piece of the reception data converted by the AD conversion unit 53 is phased and added and the focus of the ultrasound echo is narrowed is generated.

The image information data generation unit 19 generates image information data on the basis of the sound ray signal generated by the transmission and reception circuit 14. The image information data generation unit 19 has the signal processing unit 16 and the image processing unit 17 as described above.

The signal processing unit 16 generates image signal data before imaging into the ultrasound image, on the basis of the sound ray signal generated by the transmission and reception circuit 14, under the control of the probe control unit 21. More specifically, the signal processing unit 16 generates, as the image signal data before imaging, a signal representing tomographic image information regarding tissues inside the subject, by performing envelope detection processing after signal processing, for example, correcting the attenuation of the sound ray signal generated by the beam former 54 of the transmission and reception circuit 14, which is caused by the propagation distance according to the depth of the reflection position of the ultrasonic wave.

The image processing unit 17 generates the ultrasound image as the image information data generated by the image information data generation unit 19 on the basis of the image signal data generated by the signal processing unit 16, under the control of the probe control unit 21. More specifically, the image processing unit 17 raster-converts the image signal data before imaging, which is generated by the signal processing unit 16 into the image signal according to a normal television signal scanning method, performs various kinds of image processing such as brightness correction, gradation correction, sharpness correction, image size correction, refresh rate correction, scanning frequency correction, and color correction according to a display format of a monitor 34, on the image signal converted in this manner to generate the ultrasound image (ultrasound image signal), and then outputs the generated ultrasound image as the image information data to the probe-side wireless communication circuit 18.

The probe-side cine-memory 22 stores the image information data generated by the image information data generation unit 19, under the control of the probe control unit 21. More specifically, the probe-side cine-memory 22 stores the ultrasound image generated by the image processing unit 17 of the image information data generation unit 19, as the image information data in the case of the live mode. The probe-side cine-memory 22 has a memory capacity for storing ultrasound images of several tens to several hundreds of frames in a case where ultrasound images for several seconds to several tens of seconds, for example, ultrasound images of 30 frames for one second are captured.

The probe-side cine-memory 22 is a ring buffer. Thus, in a case where the ultrasound images of past frames for the number of frames corresponding to the memory capacity are stored in the probe-side cine-memory 22, instead of the ultrasound image of the oldest frame, the ultrasound image of the latest frame is sequentially stored in the probe-side cine-memory 22. In this manner, the ultrasound images of the past frames for the number of frames corresponding to the memory capacity, from the ultrasound image of the latest frame are always stored in the probe-side cine-memory 22 without being omitted.

Here, the live mode is a mode in which the ultrasound images (video) captured at a certain frame rate are sequentially displayed (real time display).

The freeze mode is a mode in which the ultrasound images (video) captured in the case of the live mode are stored in the probe-side cine-memory 22 and the ultrasound images (static image) of any frames are read and displayed from the ultrasound images (video) of the past frames stored in the probe-side cine-memory 22.

The frame adjustment unit 15 adjusts whether to output the image information data of all the frames generated by the image information data generation unit 19 or to output the image information data generated by the image information data generation unit 19 by omitting the image information data of at least a part of the frames, according to the fluctuations in the wireless transmission band by the probe-side wireless communication circuit 18, under the control of the probe control unit 21.

In the case of the live mode, the sound ray signals are sequentially generated by the transmission and reception circuit 14, and the ultrasound image of each frame are sequentially generated on the basis of the sound ray signal by the image information data generation unit 19. That is, the ultrasound images are generated at a certain frame rate.

On the other hand, the wireless transmission band by the probe-side wireless communication circuit 18 fluctuates due to disturbances such as noise, voltage fluctuation, and overload. Accordingly, in a case where the transmission speed of the wireless transmission may be decreased, or a transmission error occurs so that the wireless transmission cannot be performed, the ultrasound images of all the frames generated by the image information data generation unit 19 cannot be wirelessly transmitted in real time, in some cases.

In a case where the wireless transmission band is equal to or greater than a threshold value and the ultrasound images of all the frames generated by the image information data generation unit 19 can be wirelessly transmitted in real time without being omitted, the frame adjustment unit 15 outputs the image information data of all the frames generated by the image information data generation unit 19. In this case, the ultrasound images of all the frames generated by the image information data generation unit 19 are output from the frame adjustment unit 15 to the probe-side wireless communication circuit 18.

On the other hand, in a case where the wireless transmission band is less than the threshold value and the ultrasound images of all the frames generated by the image information data generation unit 19 cannot be wirelessly transmitted in real time, the frame adjustment unit 15 omits the ultrasound images of at least a part of the frames from among the image information data generated by the image information data generation unit 19. In this case, the ultrasound images of which at least a part of the frames are omitted are output from the frame adjustment unit 15 to the probe-side wireless communication circuit 18.

When the ultrasound image of a new frame arrives from the image information data generation unit 19 at the input of the frame adjustment unit 15, in a case where the transmission of the ultrasound image of the frame that the probe-side wireless communication circuit 18 has already received has not been completed and the ultrasound image of the new frame cannot be received, the frame adjustment unit 15 omits the ultrasound image the ultrasound image of the arrived frame.

The probe-side wireless communication circuit 18 includes an antenna for transmitting and receiving radio waves, and wirelessly transmits the image information data adjusted by the frame adjustment unit 15 in the case of the live mode, under the control of the probe control unit 21. More specifically, the probe-side wireless communication circuit 18 modulates a carrier on the basis of the ultrasound image, which is generated by the image processing unit 17 of the image information data generation unit 19 and is adjusted by the frame adjustment unit 15, to generate a transmission signal, and transmits radio waves from the antenna by supplying the transmission signal to the antenna to perform wireless transmission of the ultrasound image.

As the modulation method of the carrier, amplitude shift keying (ASK), phase shift keying (PSK), quadrature phase shift keying (QPSK), 16 quadrature amplitude modulation (16QAM), or the like is used.

In a case where the ultrasound images of all the frames generated by the image information data generation unit 19 can be wirelessly transmitted in real time without being omitted, the probe-side wireless communication circuit 18 wirelessly transmits the image information data of all the frames generated by the image information data generation unit 19. On the other hand, in a case where the wireless transmission band is less than the threshold value and the ultrasound images of all the frames generated by the image information data generation unit 19 cannot be wirelessly transmitted in real time, the probe-side wireless communication circuit 18 wirelessly transmits the ultrasound images of which at least a part of the frames are omitted by the frame adjustment unit 15.

Further, the probe-side wireless communication circuit 18 wirelessly transmits the image information data stored in the probe-side cine-memory in the case of the freeze mode.

The probe-side wireless communication circuit 18 adds time stamp information to the image information data and wirelessly transmits the image information data from the ultrasound probe 1 to the information terminal 3. The time stamp information includes an elapse time from a reference time point such as transmission start, the sequence number of the frame, and the like.

The probe control unit 21 controls each unit of the ultrasound probe 1 on the basis of a program and the like stored in advance. More specifically, the probe control unit 21 controls the transmission and reception circuit 14 such that transmission of ultrasound beams and reception of ultrasound echoes are performed on the basis of an inspection mode and a scanning method set in advance. The probe control unit 21 controls the signal processing unit 16 and the image processing unit 17 of the image information data generation unit 19 such that signal processing set in advance is performed on the sound ray signal and the image processing set in advance is performed on the image signal data.

The probe control unit 21 performs a control such that the image information data generated by the image information data generation unit 19 is stored in the probe-side cine-memory 22 in the case of the live mode. The probe control unit 21 controls the frame adjustment unit 15 to adjust frames of the image information data generated by the image information data generation unit 19 according to the fluctuation of the wireless transmission band by the probe-side wireless communication circuit 18. Further, the probe control unit 21 controls the probe-side wireless communication circuit 18 such that the image signal data is transmitted with a transmission radio field intensity set in advance.

Here, the inspection mode indicates any of inspection modes that can be used in the ultrasound system, such as a brightness (B) mode, a color Doppler (CF) mode, a power Doppler (PD) mode, a motion (M) mode, a pulse wave Doppler (PW) mode, and a continuous wave Doppler (CW) mode, and the scanning method indicates any one of scanning methods such as an electronic sector scanning method, an electronic linear scanning method, and an electronic convex scanning method.

The battery 24 is built in the ultrasound probe 1, and supplies power to each circuit of the ultrasound probe 1.

On the other hand, the information terminal 3 comprises a terminal-side wireless communication circuit 32, and a display control unit 33 and the monitor 34 are sequentially connected in series to the terminal-side wireless communication circuit 32. Further, a terminal control unit 36 is connected to the terminal-side wireless communication circuit 32 and the display control unit 33. An input device 37 is connected to the terminal control unit 36. The display control unit 33 and the terminal control unit 36 constitute a terminal-side processor 39.

The probe-side wireless communication circuit 18 of the ultrasound probe 1 and the terminal-side wireless communication circuit 32 of the information terminal 3 are connected so as to exchange information bidirectionally, and thereby the ultrasound probe 1 and the information terminal 3 are wirelessly connected by the wireless communication.

The terminal-side wireless communication circuit 32 includes an antenna for transmitting and receiving radio waves, and receives the image information data wirelessly transmitted from the probe-side wireless communication circuit 18 of the ultrasound probe 1, under the control of the terminal control unit 36. More specifically, the terminal-side wireless communication circuit 32 receives a transmission signal wirelessly transmitted from the probe-side wireless communication circuit 18 via the antenna, demodulates the received transmission signal, and outputs the ultrasound image (ultrasound image signal) as the image information data.

The display control unit 33 displays the ultrasound image on the monitor 34 on the basis of the image information data received by the terminal-side wireless communication circuit 32, under the control of the terminal control unit 36. More specifically, the display control unit 33 performs predetermined processing on the ultrasound image as the image information data to display the processed ultrasound image on the monitor 34.

The terminal control unit 36 controls each unit of the information terminal 3 on the basis of a program stored in advance and an instruction or the like of the user (operator of the ultrasound system) input from the input device 37. More specifically, the terminal control unit 36 controls the terminal-side wireless communication circuit 32 such that the reception of the transmission signal from the probe-side wireless communication circuit 18 of the ultrasound probe 1 is performed. Further, the terminal control unit 36 controls the display control unit 33 such that the ultrasound image is displayed on the monitor 34 on the basis of the image information data.

The monitor 34 displays the ultrasound image generated by the display control unit 33, and includes, for example, a display device such as a liquid crystal display (LCD).

The input device 37 is for the user to perform an input operation to input various instructions, and can be configured to comprise a keyboard, a mouse, a trackball, a touchpad, a touch panel, and the like.

Next, an operation of the ultrasound system illustrated in FIG. 1 will be described.

Figure 3:
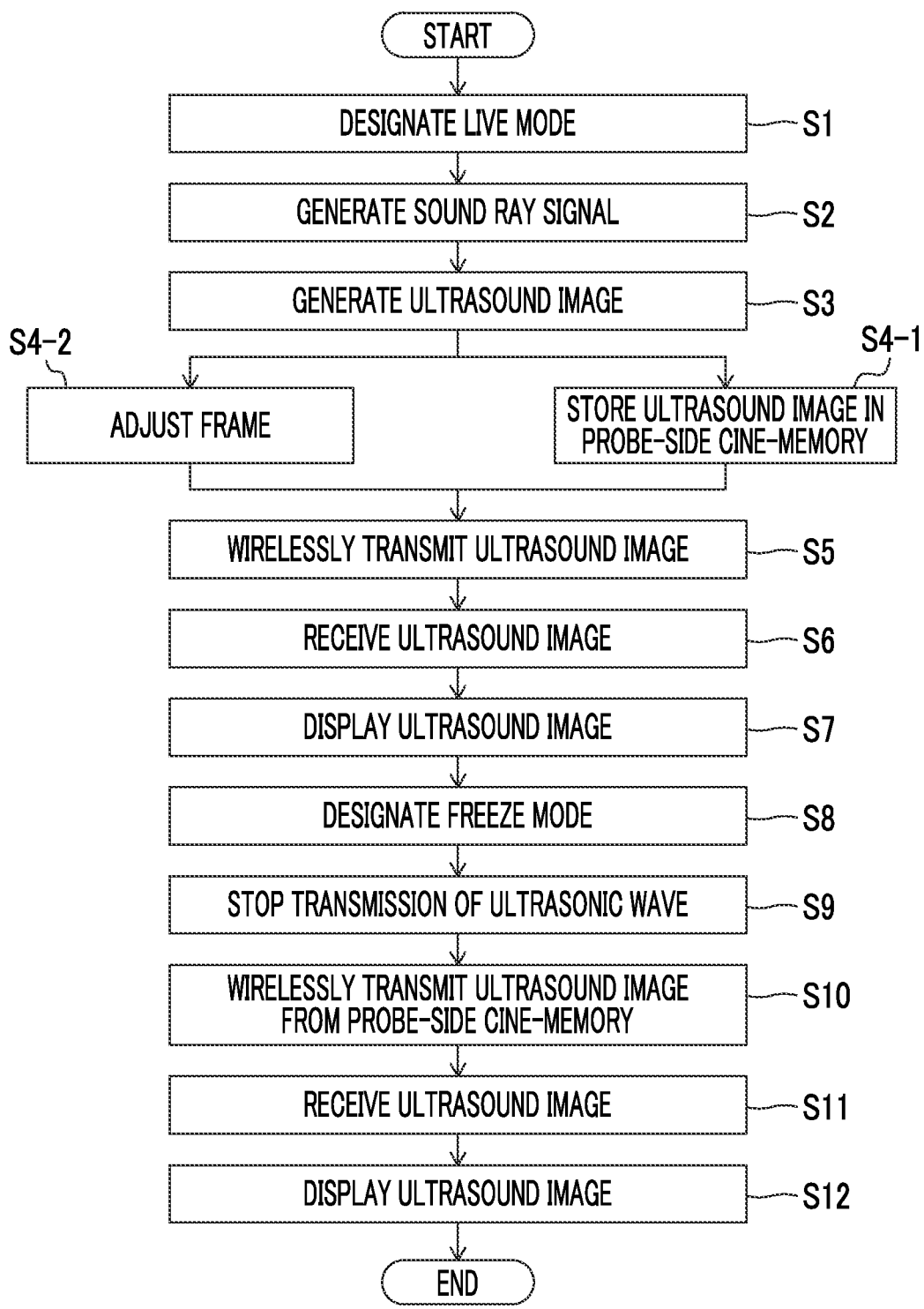
FIG. 3 is a flowchart illustrating an operation of the ultrasound system illustrated in FIG. 1.

First, the operation of the ultrasound system in the case of the live mode will be described with reference to the flowchart of FIG. 3.

In a case where the live mode is designated on the basis of the instruction from the user input from the input device 37 (Step S1), in a state where the ultrasound probe 1 is in contact with the body surface of the subject, the transmission of the ultrasonic waves from the transducer array 11 is started, and the sound ray signal is generated (Step S2).

That is, under the control of the probe control unit 21, ultrasound beams are transmitted into the subject from the plurality of transducers of the transducer array 11 according to the drive signal from the pulser 51 of the transmission and reception circuit 14.

Ultrasound echoes from the subject based on the ultrasound beams transmitted from the pulser 51 are received by each transducer of the transducer array 11, and a reception signal as an analog signal is output from each transducer of the transducer array 11, which has received the ultrasound echo.

The reception signal as the analog signal output from each transducer of the transducer array 11 is amplified by the amplification unit 52 of the transmission and reception circuit 14, and is subjected to AD conversion by the AD conversion unit 53, and thereby the reception data is acquired.

By performing the reception focusing processing on the reception data by the beam former 54, the sound ray signal is generated.

Next, the ultrasound image is generated as the image information data by the image information data generation unit 19 on the basis of the sound ray signal generated by the beam former 54 of the transmission and reception circuit 14 (Step S3).

That is, the sound ray signal generated by the beam former 54 is subjected to various kinds of signal processing by the signal processing unit 16 of the image information data generation unit 19, and the signal representing tomographic image information regarding tissues inside the subject is generated as the image signal data before imaging.

The image signal data generated by the signal processing unit 16 is raster-converted by the image processing unit 17 of the image information data generation unit 19, and is further subjected to various kinds of image processing, and the ultrasound image is generated as the image information data.

Figure 4:
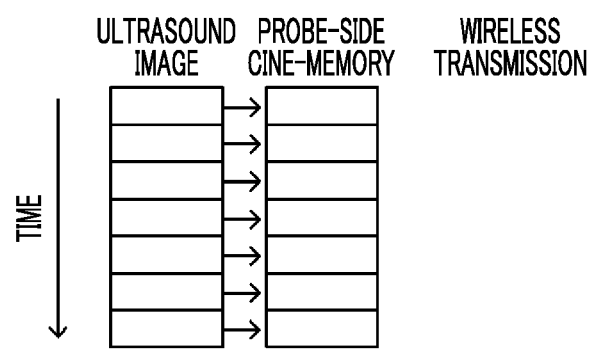
FIG. 4 is a conceptual diagram illustrating a flow of the ultrasound image in a case of a live mode of the ultrasound system illustrated in FIG. 1.

Here, FIG. 4 is a conceptual diagram illustrating a flow of the ultrasound image in the case of the live mode of the ultrasound system illustrated in FIG. 1. Each block on the left side of FIG. 4 represents the ultrasound image of each frame generated by the image processing unit 17, and each block on the right side of FIG. 4 represents each frame region in which the ultrasound image of each frame is stored, in the probe-side cine-memory 22. The vertical direction in FIG. 4 represents the flow of time, and time elapses from the upper side to the lower side.

The ultrasound image generated by the image processing unit 17 is stored in the probe-side cine-memory 22, as illustrated in FIG. 4 (Step S4-1). The ultrasound images of the past frames for the number of frames corresponding to the memory capacity, from the ultrasound image of the latest frame are always stored in the probe-side cine-memory 22 without being omitted.

The frame adjustment unit 15 adjusts whether to output the ultrasound images of all the frames generated by the image processing unit 17 or to output the ultrasound images generated by the image processing unit 17 by omitting the ultrasound images of at least a part of the frames, according to the fluctuations in the wireless transmission band by the probe-side wireless communication circuit 18 (Step S4-2).

Next, the ultrasound image adjusted by the frame adjustment unit 15 is wirelessly transmitted from the probe-side wireless communication circuit 18 to the information terminal 3 (Step S5).

Next, the ultrasound image wirelessly transmitted from the probe-side wireless communication circuit 18 of the ultrasound probe 1 is received by the terminal-side wireless communication circuit 32 under the control of the terminal control unit 36 of the information terminal 3 (Step S6).

Next, the display control unit 33 performs predetermined processing on the ultrasound image received by the terminal-side wireless communication circuit 32 to display the processed ultrasound image on the monitor 34 (Step S7).

That is, in the case of the live mode, as the image information data, the ultrasound image which is generated by the image processing unit 17 of the image information data generation unit 19 of the ultrasound probe 1 and is adjusted by the frame adjustment unit 15 is wirelessly transmitted from the probe-side wireless communication circuit 18. On the other hand, the display control unit 33 of the information terminal 3 displays the ultrasound image received by the terminal-side wireless communication circuit 32 on the monitor 34.

In the case of the live mode, even in a case where the ultrasound images of at least a part of the frames are omitted by the frame adjustment unit 15, when the ultrasound image (video) is wirelessly transmitted and displayed on the monitor 34 in real time, since it is difficult to know the omission even when the ultrasound images of at least a part of the frames are omitted, there is no particular problem.

Next, an operation of the ultrasound system in the case of the freeze mode will be described.

Figure 5:
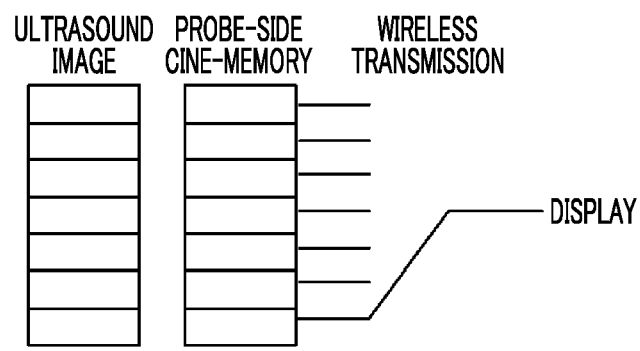
FIG. 5 is a conceptual diagram illustrating a flow of the ultrasound image in a case of a freeze mode of the ultrasound system illustrated in FIG. 1.

Here, FIG. 5 is a conceptual diagram illustrating a flow of the ultrasound image in the case of the freeze mode of the ultrasound system illustrated in FIG. 1. The configuration of each unit in FIG. 5 is similar to that in FIG. 4. In the case of the live mode, the ultrasound images of the past frames for the number of frames corresponding to the memory capacity, from the ultrasound image of the latest frame at the time point when the freeze mode is designated are stored in the probe-side cine-memory 22 without being omitted.

In a case where the freeze mode is designated on the basis of the user's instruction input from the input device 37 (Step S8), the transmission of the ultrasonic waves from the transducer array 11 is stopped (Step S9).

In this case, as illustrated in FIG. 5, as the image information data, the ultrasound images of the past frames stored in the probe-side cine-memory 22 are read and wirelessly transmitted from the probe-side wireless communication circuit 18 (Step S10).

Next, the ultrasound image wirelessly transmitted from the probe-side wireless communication circuit 18 is received by the terminal-side wireless communication circuit 32 (Step S11).

Next, the display control unit 33 displays the ultrasound image of the past frame received by the terminal-side wireless communication circuit 32 on the monitor 34 (Step S12).

In the example illustrated in FIG. 5, the ultrasound image stored in the lowermost frame region of the probe-side cine-memory 22 is wirelessly transmitted, and is displayed on the monitor 34.

In the ultrasound system of the first embodiment, in the case of the live mode, even in a case where the ultrasound images of at least a part of frames are omitted by the frame adjustment unit 15, the ultrasound images of the past frames for the number of frames corresponding to the memory capacity from the time point when the freeze mode is designated are stored in the probe-side cine-memory 22. Therefore, in the case of the freeze mode, the ultrasound images of any frames stored in the probe-side cine-memory 22 can be displayed on the monitor 34 without being omitted, and the ultrasound images that are continuously and correctly changed along the time axis can be displayed on the monitor 34.

In the freeze mode, in a case where the ultrasound images (video) are displayed on the monitor 34, since the ultrasound images are required to be wirelessly transmitted in real time similar to the case of the live mode, the ultrasound images of at least a part of frames are omitted in some cases. On the other hand, in a case where the ultrasound image (static image) is displayed on the monitor 34, since there is time to spare for the wireless transmission unlike the case of wirelessly transmitting the ultrasound images in real time, the ultrasound images of frames to be displayed on the monitor 34 can be wirelessly transmitted without being omitted.

Next, a modification example of the ultrasound system of the first embodiment illustrated in FIG. 1 will be described.

Figure 6:
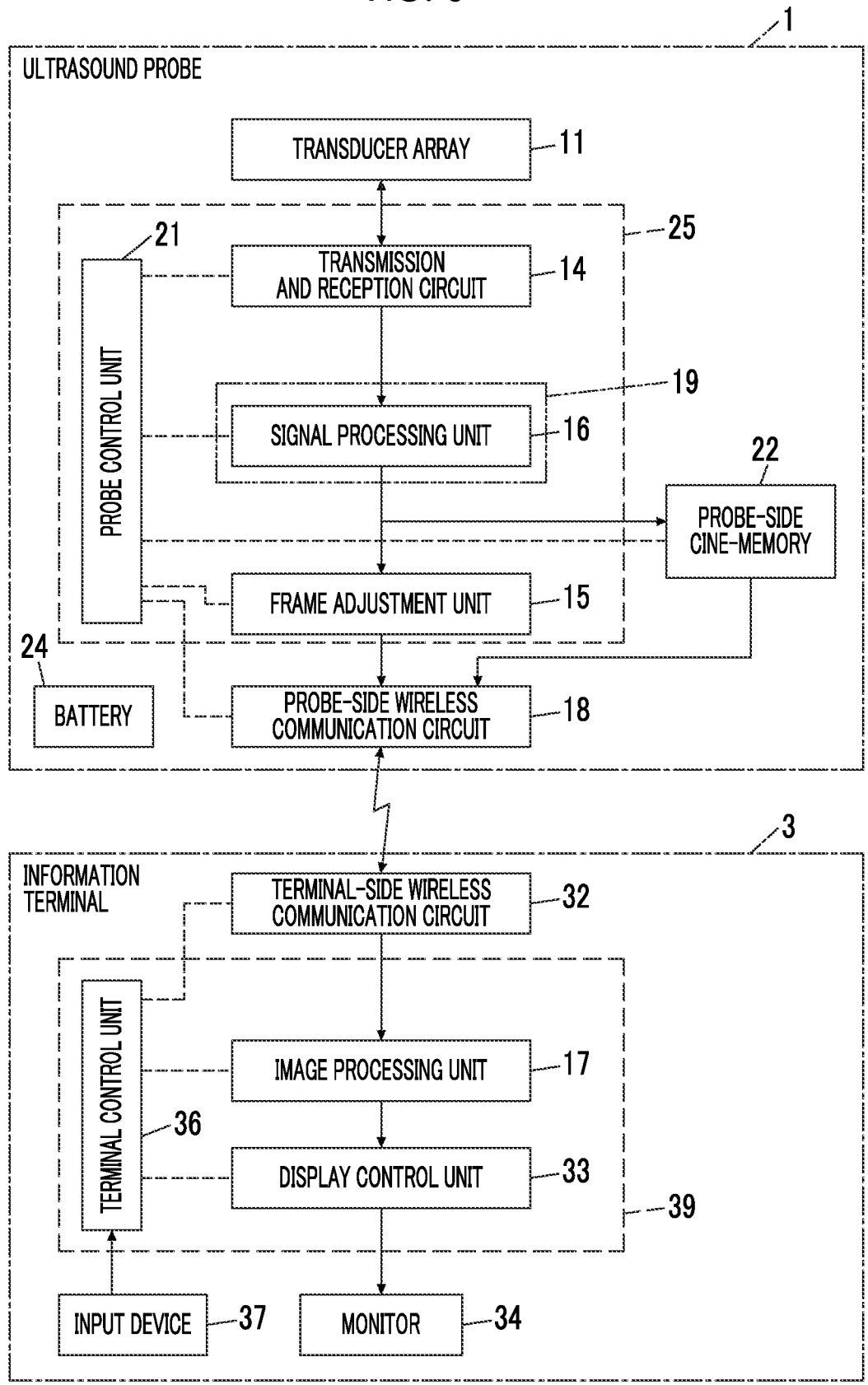
FIG. 6 is a block diagram illustrating a configuration of a modification example of the ultrasound system of the first embodiment.

FIG. 6 illustrates a block diagram illustrating a configuration of the modification example of the ultrasound system of the first embodiment. Since the ultrasound system illustrated in FIG. 6 is the same as the ultrasound system illustrated in FIG. 1 except that the image information data generation unit 19 of the ultrasound probe 1 includes only the signal processing unit 16 and the information terminal 3 further includes the image processing unit 17, the same reference numerals are given to the same constituents, and the detailed description thereof will be omitted.

In the ultrasound probe 1 of the ultrasound system illustrated in FIG. 6, the frame adjustment unit 15 and the probe-side wireless communication circuit 18 are sequentially connected in series to the signal processing unit 16. Further, the probe-side cine-memory 22 is connected to the signal processing unit 16.

On the other hand, in the information terminal 3, the image processing unit 17, the display control unit 33, and the monitor 34 are sequentially connected in series to the terminal-side wireless communication circuit 32. The terminal control unit 36 is connected to the image processing unit 17.

In the ultrasound probe 1, the signal processing unit 16 generates the image signal data before imaging into the ultrasound image, as the image information data generated by the image information data generation unit 19 on the basis of the sound ray signal generated by the transmission and reception circuit 14.

The frame adjustment unit 15 and the probe-side cine-memory 22 process, as the image information data, the image signal data generated by the signal processing unit 16 instead of the ultrasound image.

Further, the image processing unit 17 generates the ultrasound image on the basis of the image signal data received by the terminal-side wireless communication circuit 32, as the image information data under the control of the terminal control unit 36.

The display control unit 33 displays the ultrasound image generated by the image processing unit 17 on the monitor 34 under the control of the terminal control unit 36. More specifically, the display control unit 33 performs predetermined processing on the ultrasound image to display the processed ultrasound image on the monitor 34.

Figure 7:
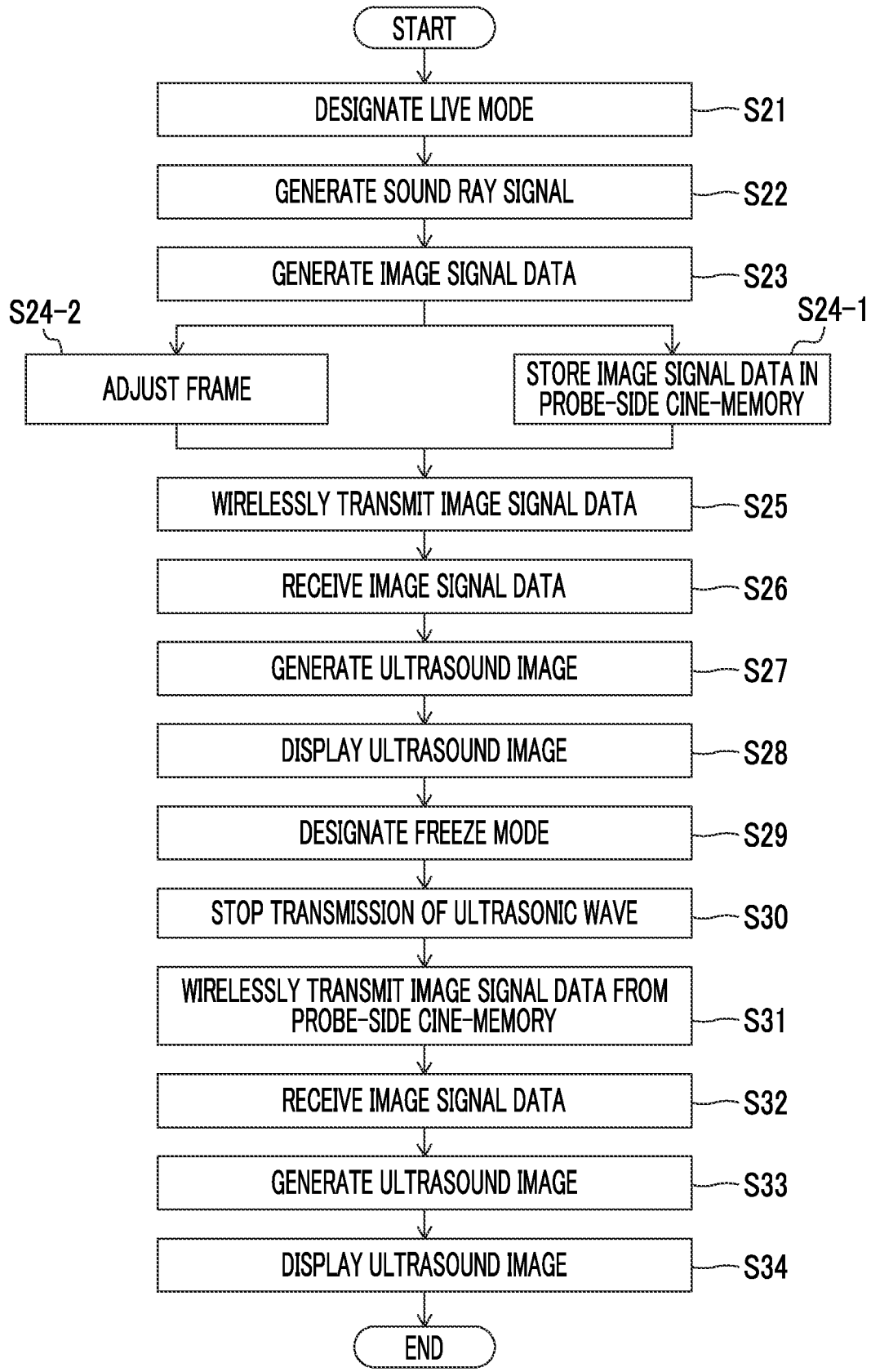
FIG. 7 is a flowchart illustrating an operation of the ultrasound system illustrated in FIG. 6.

Next, the operation of the ultrasound system illustrated in FIG. 6 will be described with reference to the flowchart illustrated in FIG. 7.

First, in the case of the live mode (Step S21), the operation until the sound ray signal is generated by the transmission and reception circuit 14 (Step S22) is the same as that (Steps S1 and S2) in the ultrasound system illustrated in FIG. 1.

Next, as the image information data, the image signal data is generated by the signal processing unit 16 (Step S23).

The image signal data generated by the signal processing unit 16 is stored in the probe-side cine-memory 22 as illustrated in FIG. 4 (Step S24-1). The image signal data of the past frames for the number of frames corresponding to the memory capacity, from the image signal data of the latest frame is stored in the probe-side cine-memory 22 without being omitted.

The frame adjustment unit 15 adjusts whether to output the image signal data of all the frames generated by the signal processing unit 16 or to output the image signal data generated by the signal processing unit 16 by omitting the image signal data of at least a part of the frames, according to the fluctuations in the wireless transmission band by the probe-side wireless communication circuit 18 (Step S24-2).

Next, the image signal data adjusted by the frame adjustment unit 15 is wirelessly transmitted from the probe-side wireless communication circuit 18 to the information terminal 3 (Step S25).

Next, the image signal data wirelessly transmitted from the probe-side wireless communication circuit 18 of the ultrasound probe 1 is received by the terminal-side wireless communication circuit 32 under the control of the terminal control unit 36 of the information terminal 3 (Step S26).

The image signal data received by the terminal-side wireless communication circuit 32 is raster-converted by the image processing unit 17, and is further subjected to various kinds of image processing, and the ultrasound image is generated (Step S27).

Next, the display control unit 33 performs predetermined processing on the ultrasound image generated by the image processing unit 17 to display the processed ultrasound image on the monitor 34 (Step S28).

That is, in the case of the live mode, as the image information data, the image signal data which is generated by the signal processing unit 16 of the ultrasound probe 1 and is further adjusted by the frame adjustment unit 15 is wirelessly transmitted from the probe-side wireless communication circuit 18. On the other hand, the ultrasound image is generated by the image processing unit 17 on the basis of the image signal data received by the terminal-side wireless communication circuit 32 of the information terminal 3, and the display control unit 33 displays the ultrasound image generated by the image processing unit 17 on the monitor 34.

Next, an operation of the ultrasound system in the case of the freeze mode will be described.

In the case of the freeze mode (Step S29), the operation until the transmission of the ultrasonic waves is stopped (Step S30) is the same as that (Steps S8 and S9) in the ultrasound system illustrated in FIG. 1.

As illustrated in FIG. 5, the past image signal data stored in the probe-side cine-memory 22 of the ultrasound probe 1 is read and wirelessly transmitted from the probe-side wireless communication circuit 18 (Step S31).

Next, the image signal data wirelessly transmitted by the probe-side wireless communication circuit 18 is received by the terminal-side wireless communication circuit 32 of the information terminal 3 (Step S32).

The ultrasound image is generated by the image processing unit 17 on the basis of the image signal data received by the terminal-side wireless communication circuit 32 (Step S33).

Next, the display control unit 33 displays the ultrasound image generated by the image processing unit 17 on the monitor 34 (Step S34).

In the embodiment, in the information terminal 3, since the ultrasound image is generated by performing the image processing on the image signal data, there is an advantage that image processing conditions such as gain can be freely changed according to the display characteristics of the monitor 34 after the ultrasound image is displayed on the monitor 34.

Next, an ultrasound system of a second embodiment will be described.

Figure 8:
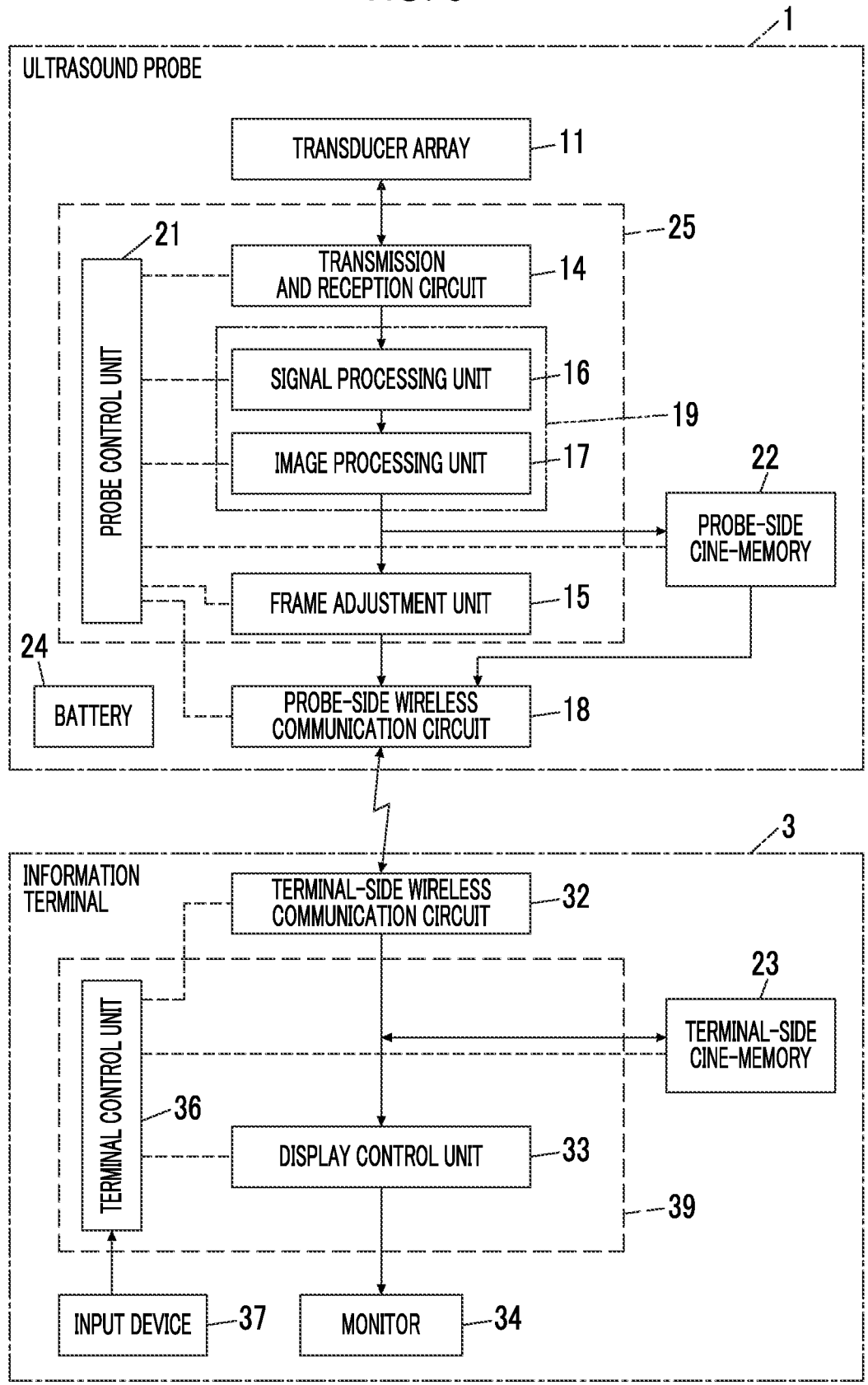
FIG. 8 is a block diagram illustrating a configuration of an ultrasound system of a second embodiment according to the present invention.

FIG. 8 illustrates a block diagram illustrating a configuration of the ultrasound system of the second embodiment according to the present invention. Since the ultrasound system illustrated in FIG. 8 is the same as the ultrasound system illustrated in FIG. 1 except that the information terminal 3 further includes a terminal-side cine-memory 23, the same reference numerals are given to the same constituents, and the detailed description thereof will be omitted.

In the information terminal 3 of the ultrasound system illustrated in FIG. 8, the terminal-side cine-memory 23 is bidirectionally connected to the terminal-side wireless communication circuit 32. Further, the terminal control unit 36 is connected to the terminal-side cine-memory 23.

The terminal-side cine-memory 23 stores the image information data received by the terminal-side wireless communication circuit 32, under the control of the terminal control unit 36. More specifically, the terminal-side cine-memory 23 stores the ultrasound image received by the terminal-side wireless communication circuit 32, as the image information data in the case of the live mode. The terminal-side cine-memory 23 has the same memory capacity as that of the probe-side cine-memory 22, and is operated in synchronization with the probe-side cine-memory 22.

The terminal-side cine-memory 23 is a ring buffer. Thus, in a case where the ultrasound images of past frames for the number of frames corresponding to the memory capacity are stored in the terminal-side cine-memory 23, instead of the ultrasound image of the oldest frame, the ultrasound image of the latest frame is stored in the terminal-side cine-memory 23. In this manner, the ultrasound images of the past frames for the number of frames corresponding to the memory capacity, from the ultrasound image of the latest frame are always stored in the terminal-side cine-memory 23.

Figure 9:
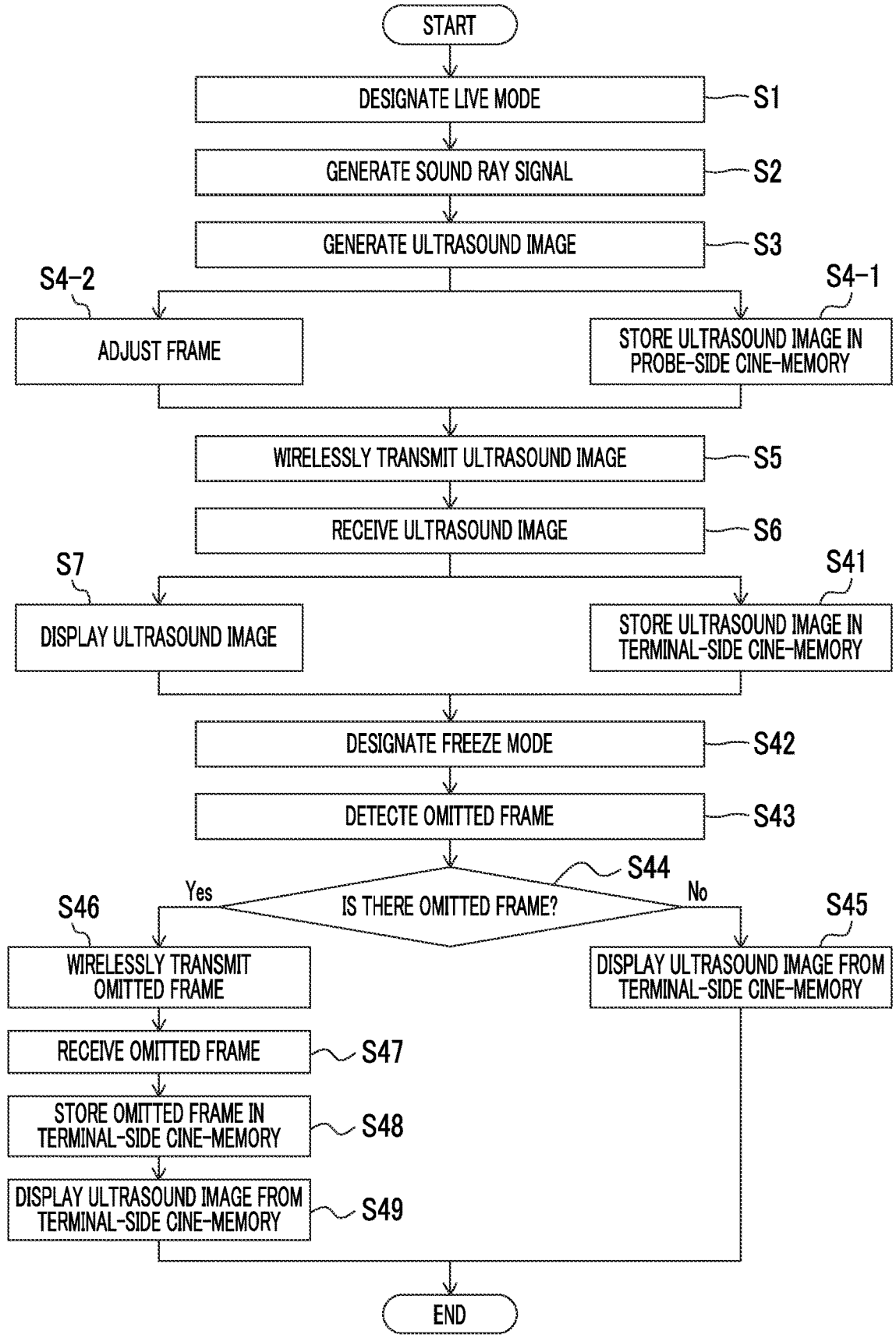
FIG. 9 is a flowchart illustrating an operation of the ultrasound system illustrated in FIG. 8.

Next, the operation of the ultrasound system illustrated in FIG. 8 will be described with reference to the flowchart illustrated in FIG. 9.

First, in the case of the live mode, the ultrasound system is operated in the same manner as the ultrasound system illustrated in FIG. 1 (Steps S1 to S12), the ultrasound image, which is adjusted by the frame adjustment unit 15 of the ultrasound probe 1, wirelessly transmitted by the probe-side wireless communication circuit 18 of the ultrasound probe 1, and is received by the terminal-side wireless communication circuit 32 of the information terminal 3, is displayed on the monitor 34 by the display control unit 33, and is further stored in the terminal-side cine-memory 23 (Step S41).

In a case where the ultrasound images of all the frames generated by the image information data generation unit 19 can be wirelessly transmitted in real time without being omitted, the ultrasound images of the past frames for the number of frames corresponding to the memory capacity, from the ultrasound image of the latest frame are stored in the terminal-side cine-memory 23 without being omitted.

Figure 10:
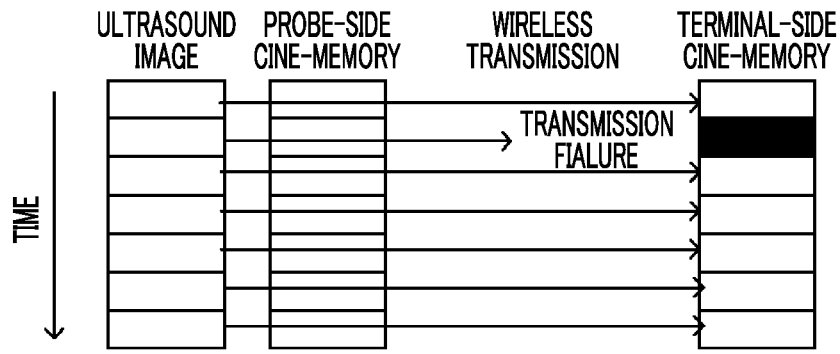
FIG. 10 is a conceptual diagram illustrating a flow of the ultrasound image in a case of a live mode of the ultrasound system illustrated in FIG. 8.

On the other hand, in a case where the ultrasound images of all the frames generated by the image information data generation unit 19 cannot be wirelessly transmitted in real time, in other words, in a case where wireless transmission fails, the ultrasound images of which at least a part of the frames are omitted are stored in the terminal-side cine-memory 23. As illustrated in FIG. 10, for example, in a case where the wireless transmission of the ultrasound image of the second frame from the upper side fails, the ultrasound images of which the second frame from the upper side is omitted are stored in the terminal-side cine-memory 23.

In the case of the freeze mode (Step S42), at least a part of frames of the ultrasound images omitted by the frame adjustment unit 15 is detected from the ultrasound images stored in the terminal-side cine-memory 23 (Step S43).

As a result, in a case where the ultrasound images of the past frames for the number of frames corresponding to the memory capacity, from the ultrasound image of the latest frame are stored in the terminal-side cine-memory 23 without being omitted (No in Step S44), the display control unit 33 displays the ultrasound images of the past frames stored in the terminal-side cine-memory 23 on the monitor 34 (Step S45).

In this manner, the ultrasound image of any past frame from among the ultrasound images stored in the terminal-side cine-memory 23 can be displayed on the monitor 34.

Figure 11:
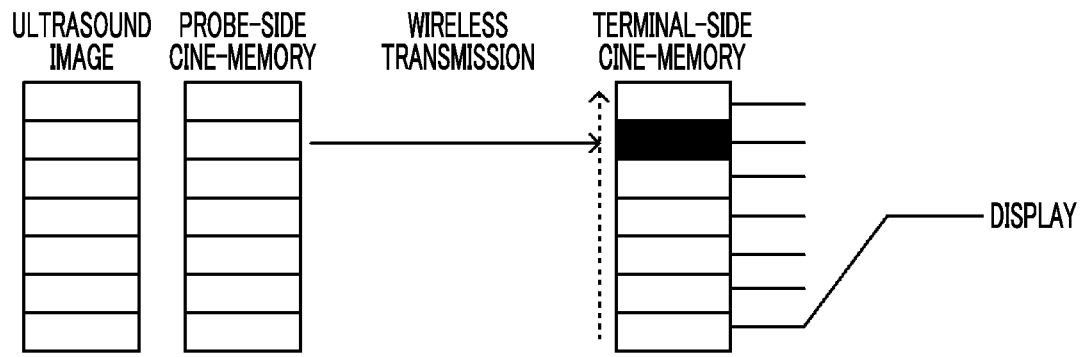
FIG. 11 is a conceptual diagram illustrating a flow of the ultrasound image in a case of a freeze mode of the ultrasound system illustrated in FIG. 8.

On the other hand, as illustrated in FIG. 10, in a case where the ultrasound images of which at least a part of frames is omitted are stored (Yes in Step S44), the ultrasound images of the at least a part of frames omitted by the frame adjustment unit 15 are read from the probe-side cine-memory 22 and are wirelessly transmitted from the probe-side wireless communication circuit 18 on the basis of the detected at least a part of frames of the ultrasound images as illustrated in FIG. 11 (Step S46).

Next, the ultrasound images of the omitted at least a part of frames wirelessly transmitted by the probe-side wireless communication circuit 18 are received by the terminal-side wireless communication circuit 32 (Step S47).

Next, the ultrasound images of the omitted at least a part of frames received by the terminal-side wireless communication circuit 32 are stored in the terminal-side cine-memory (Step S48).

Next, the display control unit 33 reads and displays the ultrasound images stored in the terminal-side cine-memory 23 on the monitor 34 (Step S49).

In the ultrasound system of the second embodiment, in the case of the freeze mode, the ultrasound image of the omitted frame is wirelessly transmitted from the probe-side cine-memory 22 and is stored in the terminal-side cine-memory 23. That is, the ultrasound images of the past frames for the number of frames corresponding to the memory capacity, from the ultrasound image of the latest frame at the time point when the freeze mode is designated are stored in the terminal-side cine-memory 23 without being omitted. Therefore, the display control unit 33 can display the ultrasound image of any past frame from among the ultrasound images stored in the terminal-side cine-memory 23, on the monitor 34 without inquiring about the ultrasound image of the frame to be displayed on the monitor 34 to the ultrasound probe 1 side and therefore without requiring the turnaround time for the inquiry. For example, even in a case where the ultrasound image of one frame is sequentially displayed frame by frame toward the ultrasound image of the past or latest frame, smooth frame advance can be achieved without the delay due to the wireless transmission, and it is possible to significantly improve the operability for the user.

As described above, time stamp information is attached to the ultrasound image wirelessly transmitted from the ultrasound probe 1 to the information terminal 3. Thus, it is possible to check whether there is the ultrasound image of the omitted frame in the terminal-side cine-memory 23 on the basis of the time stamp information. For example, in a case where the frame sequence numbers of the ultrasound images of the frames stored in the terminal-side cine-memory 23 are consecutive, it can be seen that there is no omitted frame of the ultrasound image. On the other hand, in a case where the frame sequence numbers are not consecutive, it can be seen that there is an omitted frame of the ultrasound image, and it is also check the frame sequence number of the ultrasound image of the omitted frame.

The order of detecting the omitted frame of the ultrasound image is not particularly limited, but detection of at least a part of frames of the ultrasound images omitted by the frame adjustment unit 15 is sequentially performed for the frame of the ultrasound image pointed to by a scan pointer, toward the past frame of the ultrasound image from the frame of the ultrasound image of the terminal-side cine-memory 23, which corresponds to the ultrasound image being displayed on the monitor 34 among the ultrasound images stored in the terminal-side cine-memory 23.

Further, in a case where the frame of the ultrasound image pointed to by the scan pointer is moved to the past frame of the ultrasound image earlier than the frame of the ultrasound image being displayed on the monitor 34 on the basis of the instruction input from the input device 37, the frame of the ultrasound image pointed to by the scan pointer is changed to the moved past frame of the ultrasound image, and the detection of at least a part of frames of the ultrasound images omitted by the frame adjustment unit 15 is sequentially performed for the frame of the ultrasound image pointed to by the scan pointer toward the latest frame of the ultrasound image from the past frame of the ultrasound image which has been pointed to by the scan pointer and changed.

In a case where the frame of the ultrasound image pointed to by the scan pointer reaches the latest frame of the ultrasound image, the frame of ultrasound image pointed to by the scan pointer is changed to the moved past frame of the ultrasound image, and the detection of at least a part of frames of the ultrasound images omitted by the frame adjustment unit 15 is sequentially performed for the frame of the ultrasound image pointed to by the scan pointer, from the changed past frame of the ultrasound image pointed to by the scan pointer toward the past frame of the ultrasound image which is further earlier than the changed past frame of the ultrasound image.

In the case of the freeze mode, from among the ultrasound images stored in the terminal-side cine-memory 23, the ultrasound image (static image) of the latest frame at the time point when the freeze mode is designated is displayed on the monitor 34, and the ultrasound image of any past frame going back from the ultrasound image of the latest frame is displayed, or the ultrasound image of one frame can be sequentially displayed frame by frame (cine-scrolling) toward the ultrasound image of the past or latest frame as described above.

After the ultrasound image of any frame is displayed on the monitor 34, the ultrasound images (video) from the ultrasound image of any frame toward the ultrasound image of the latest frame can be reproduced and displayed (cine reproduction).

Therefore, when the ultrasound image of any past frame is displayed, it is required to sequentially detect the omitted frame of the ultrasound image from the ultrasound image of the latest frame toward the ultrasound image of the past frame. When the ultrasound images (video) are reproduced from the ultrasound image of any frame, it is required to sequentially perform detection in the reproduction direction, that is, from the ultrasound image of any frame toward the ultrasound image of the latest frame. Further, as described above, since the ultrasound image of one frame can be sequentially displayed frame by frame, the detection of the frame of the ultrasound image in the vicinity of the frame of the ultrasound image corresponding to the ultrasound image being displayed on the monitor 34 has the highest priority.

In a case where there is the ultrasound image of the omitted frame in the terminal-side cine-memory 23, for example, the frame sequence number of the ultrasound image of the omitted frame is wirelessly transmitted from the terminal-side wireless communication circuit 32 to the probe-side wireless communication circuit 18. The ultrasound image of the frame corresponding to the frame sequence number received from the terminal-side wireless communication circuit 32 is read from the probe-side cine-memory 22, and is wirelessly transmitted by the probe-side wireless communication circuit 18.

Alternatively, instead of sequentially detecting the omitted frame of the ultrasound image in the terminal-side cine-memory 23, in the case of the live mode, the frame adjustment unit 15 may generate an omitted frame list for managing at least a part of frames of the ultrasound images omitted from the ultrasound images wirelessly transmitted by the probe-side wireless communication circuit 18.

In this case, in the case of the freeze mode, on the basis of the omitted frame list generated by the frame adjustment unit 15, the ultrasound images of at least a part of frames omitted by the frame adjustment unit 15 are read from the probe-side cine-memory 22, and are wirelessly transmitted from the probe-side wireless communication circuit 18.

The timing when the ultrasound image of the omitted frame is wirelessly transmitted from the probe-side cine-memory 22 to the terminal-side cine-memory 23 is not particularly limited as long as the ultrasound image of the omitted frame is not displayed on the monitor 34. However, the ultrasound images of at least a part of frames omitted by the frame adjustment unit 15 can be read from the probe-side cine-memory 22, and wirelessly transmitted from the probe-side wireless communication circuit 18, immediately after the freeze mode is designated, for example.

Alternatively, on the basis of the instruction input from the input device 37, a frame in the vicinity of, for example, a frame that is one to three frames apart from at least a part of frames of the ultrasound images omitted by the frame adjustment unit 15 is designated from among the ultrasound images stored in the terminal-side cine-memory 23, and the ultrasound images of at least a part of frames omitted by the frame adjustment unit 15 may be read from the probe-side cine-memory 22, and wirelessly transmitted from the probe-side wireless communication circuit 18 immediately after the ultrasound image is displayed on the monitor 34 on the basis of the ultrasound image of the designated vicinity frame.

As described above, the memory capacity of the probe-side cine-memory 22 and the memory capacity of the terminal-side cine-memory 23 are the same, and in the case of the freeze mode, the probe-side cine-memory 22 is operated in synchronization with the terminal-side cine-memory 23. As a result, in the case of the freeze mode, the ultrasound image of each frame that is exactly the same as the ultrasound image of each frame stored in the probe-side cine-memory 22 is finally stored in the terminal-side cine-memory 23.

As the information terminal 3 of the ultrasound system of the present invention, not only a dedicated information terminal but also a commercially available tablet terminal or the like can be used. Thus, it is assumed that the memory capacity of the probe-side cine-memory 22 and the memory capacity of the terminal-side cine-memory 23 are different from each other.

In this case, the number of frames of the ultrasound images to be stored in one of the probe-side cine-memory 22 and the terminal-side cine-memory 23, which has the larger memory capacity, is decided in accordance with the one of the probe-side cine-memory 22 and the terminal-side cine-memory 23, which has the smaller memory capacity, and thereby the number of frames of the ultrasound images to be stored in the probe-side cine-memory 22 and the number of frames of the ultrasound images to be stored in the terminal-side cine-memory 23 can be matched.

In the ultrasound system of the second embodiment, in the case of the live mode, the ultrasound images of all the frames generated by the image information data generation unit 19 are stored in the probe-side cine-memory 22, but in the case of the freeze mode, the ultrasound images of the frames wirelessly transmitted from the probe-side wireless communication circuit 18 and the ultrasound images of the frames for which reception confirmation is notified from the information terminal 3 may be deleted from the probe-side cine-memory 22.

For example, as the transmission method of the wireless communication, User Datagram Protocol (UDP) and Transmission Control Protocol (TCP) of the Internet Protocol (IP) are known. In the case of the UDP, since reception confirmation is not performed at the protocol level, in a case where reception confirmation is notified from the terminal-side wireless communication circuit 32, the ultrasound image of the frame corresponding to the notification can be deleted from the probe-side cine-memory 22. In the case of the TCP, since reception confirmation is performed at the protocol level, at the time point of the wireless transmission from the probe-side wireless communication circuit 18, the corresponding ultrasound image of the frame can be deleted from the probe-side cine-memory 22.

In this case, in the case of the freeze mode, the probe-side cine-memory 22 generates a free space management list for managing a free space of the probe-side cine-memory 22 to manage the free space.

That is, in the case of the freeze mode, the frame region of the probe-side cine-memory 22 where the ultrasound image of the frame deleted from the probe-side cine-memory 22 is stored is the free space in the free space management list. In the case of the next live mode, the ultrasound image of each frame generated by the image processing unit 17 is sequentially stored from the frame region of the probe-side cine-memory 22 corresponding to the head free space of the free space management list.

Figure 12:
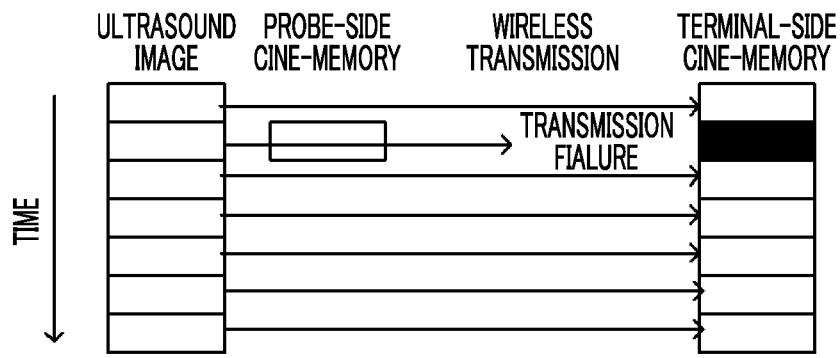
FIG. 12 is another conceptual diagram illustrating a flow of the ultrasound image in the case of the live mode of the ultrasound system illustrated in FIG. 8.
Figure 13:
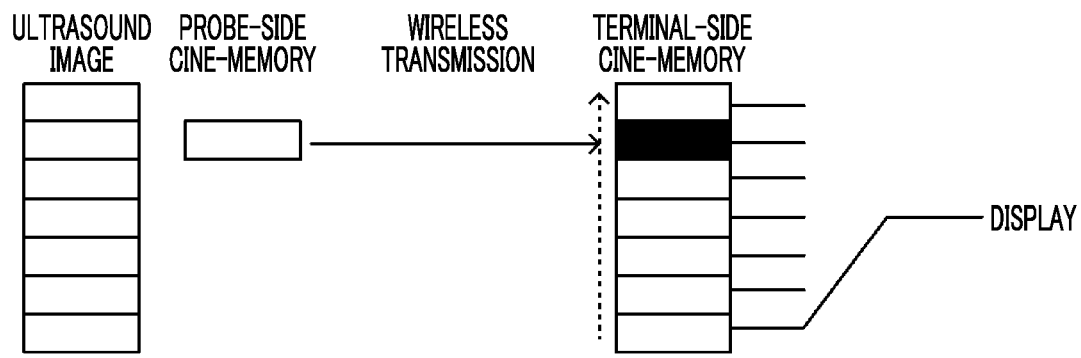
FIG. 13 is another conceptual diagram illustrating a flow of the ultrasound image in the case of the freeze mode of the ultrasound system illustrated in FIG. 8.

Further, in the ultrasound system of the second embodiment, instead of storing the ultrasound image of each frame generated by the image information data generation unit 19 in the probe-side cine-memory 22 once, as illustrated in FIGS. 12 and 13, in the case of the live mode, only the ultrasound images of at least a part of frames omitted by the frame adjustment unit 15 may be stored in the probe-side cine-memory 22, and in the case of the freeze mode, the ultrasound image of the frame for which reception confirmation at the time of the transmission from the probe-side cine-memory 22 to the terminal-side cine-memory 23 is notified from the information terminal 3 may be deleted from the probe-side cine-memory 22.

In the case of the live mode, the ultrasound image of the frame deleted from the terminal-side cine-memory 23 is deleted from the probe-side cine-memory 22. In the case of the live mode, the ultrasound image of the frame deleted from the terminal-side cine-memory 23 is an ultrasound image of the past frame earlier than the ultrasound images of the past frames for the number of frames corresponding to the memory capacity of the terminal-side cine-memory 23 from the ultrasound image of the latest frame, and is not displayed on the monitor 34. Therefore, the ultrasound image is also deleted from the probe-side cine-memory 22.

In this manner, by deleting the ultrasound image of the frame that is no longer needed from the probe-side cine-memory 22, as illustrated in FIGS. 12 and 13, only the ultrasound image of the frame corresponding to the ultrasound image of the omitted frame is stored in the probe-side cine-memory 22. Therefore, it is possible to significantly reduce the memory capacity of the probe-side cine-memory 22 required in the case of the freeze mode, and it is possible to significantly improve the utilization efficiency of the probe-side cine-memory 22. Since the ultrasound images stored in the probe-side cine-memory 22 are sequentially deleted, even in a case where the wireless communication is performed for a long period of time, the probe-side cine-memory 22 is never full unless the wireless communication environment has a lot of disturbance.

Here, reading the ultrasound image from the probe-side cine-memory 22 by wireless transmission is usually faster than the speed at which the ultrasound image is generated by the image processing unit 17. However, in a case where a transmission error occurs due to the influence of disturbance or the like and the wireless transmission retry occurs, since it takes time to retry the wireless transmission, as the ultrasound images of the omitted frames, the ultrasound images of the plurality of frames are stored in the probe-side cine-memory 22. Therefore, it is desirable that the probe-side cine-memory 22 has a memory capacity capable of storing the ultrasound images (video) for one second or longer.

Figure 14:
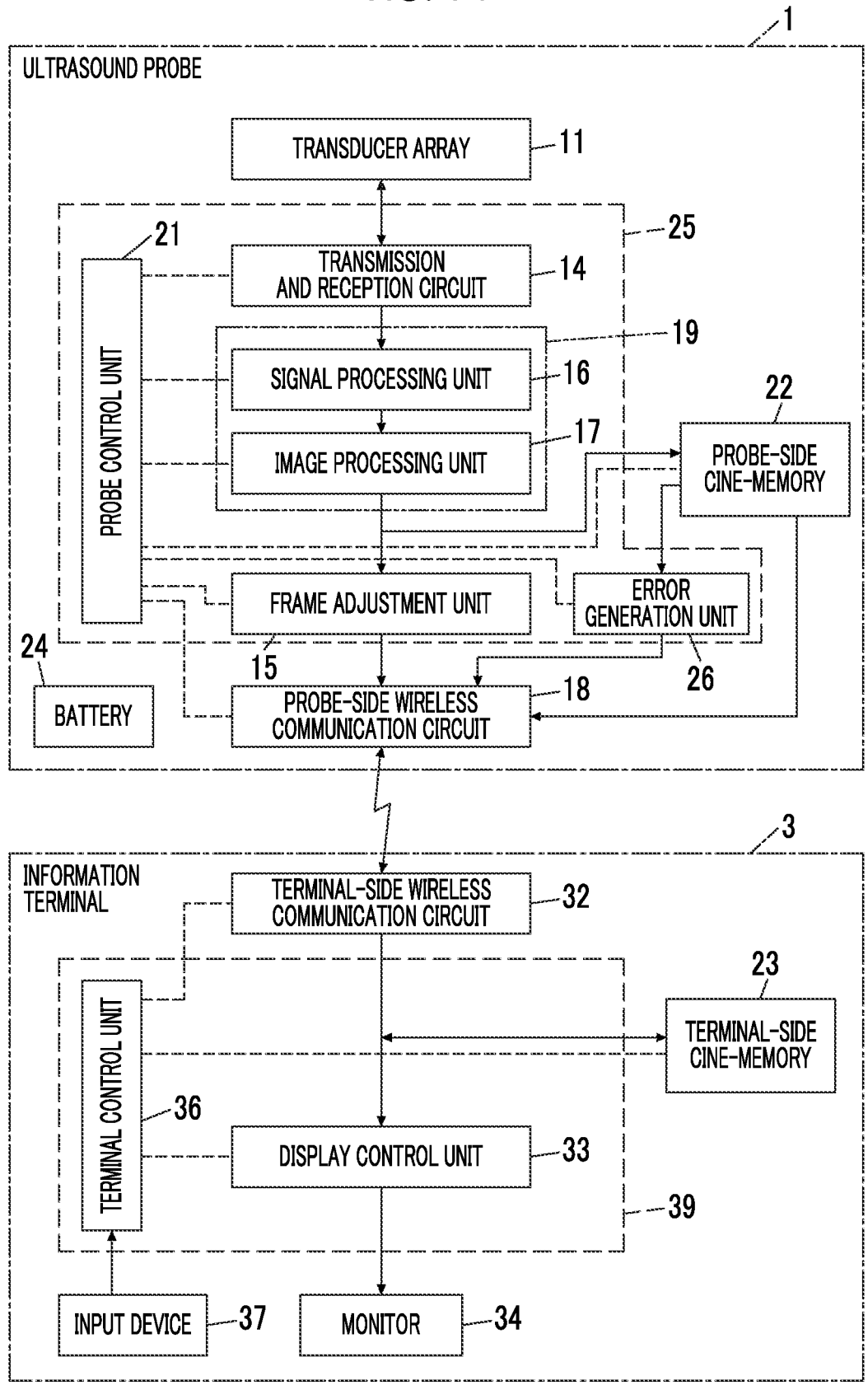
FIG. 14 is another block diagram illustrating a configuration of the ultrasound system of the second embodiment.

On the other hand, in a case where the free space of the probe-side cine-memory 22 runs out, it can be determined that there is a lot of disturbance so that the wireless communication environment is inappropriate. Correspondingly, as illustrated in FIG. 14, it is desirable that the ultrasound probe 1 further includes an error generation unit 26. The error generation unit 26 constitutes a part of the probe-side processor 25, and is connected to the probe-side cine-memory 22. The probe-side wireless communication circuit 18 is connected to the error generation unit 26, and the probe control unit 21 is connected to the error generation unit 26.

In the case of the live mode, the error generation unit 26 issues an error when the probe-side cine-memory 22 is filled with the ultrasound images of the omitted frames. For example, the error issued by the error generation unit 26 is wirelessly transmitted from the probe-side wireless communication circuit 18, and is received by the terminal-side wireless communication circuit 32, and a message corresponding to the error is displayed on the monitor 34 by the display control unit 33. Alternatively, the error issued by the error generation unit 26 may be output from the speaker as a voice, or the display of the message of the error and the output of the voice may be simultaneously performed.

In this manner, it is possible for user to grasp that the wireless communication environment is bad and a transmission error occurs frequently.

Next, a modification example of the ultrasound system of the second embodiment illustrated in FIG. 8 will be described.

Figure 15:
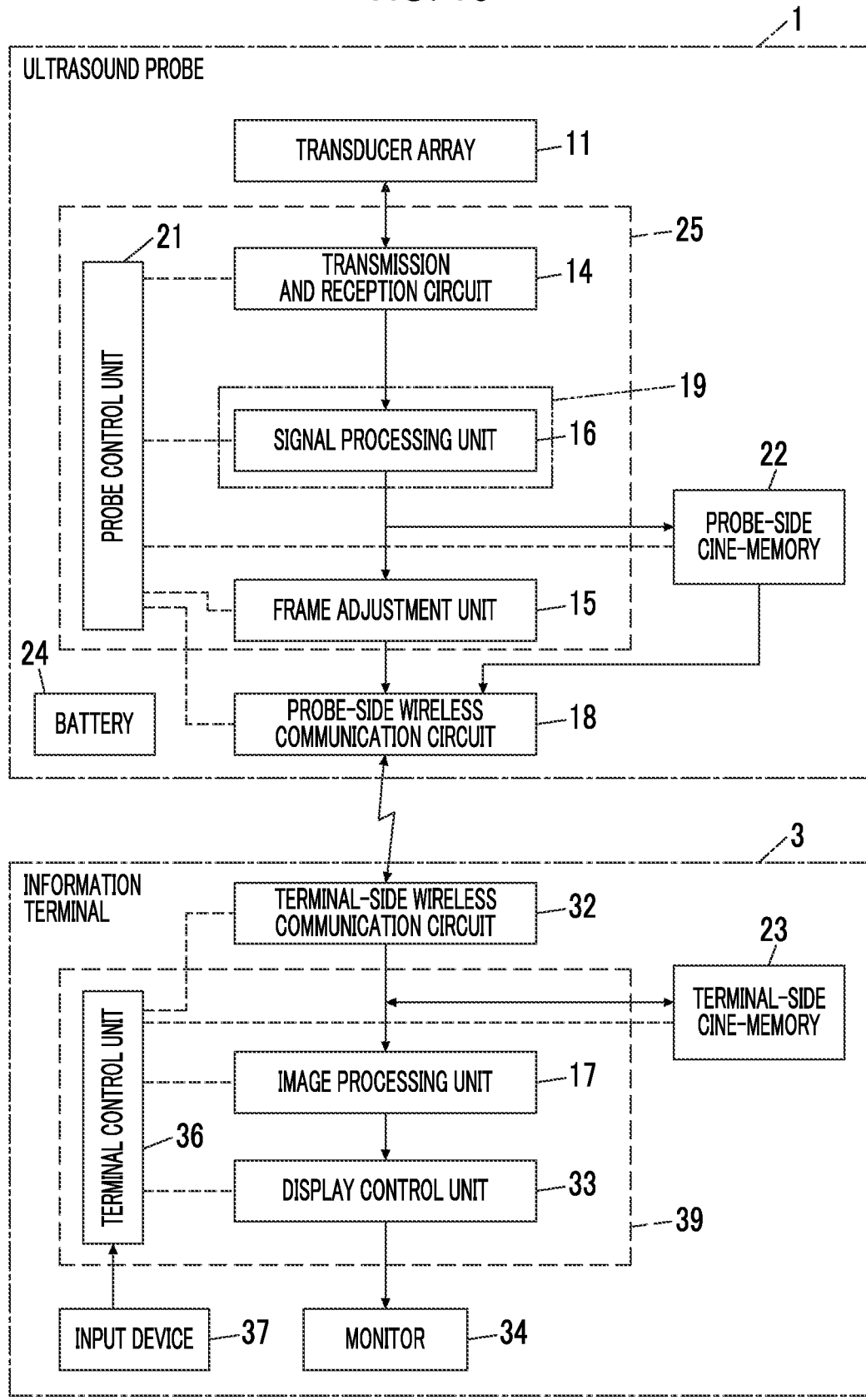
FIG. 15 is a block diagram illustrating a configuration of a modification example of the ultrasound system of the second embodiment.

FIG. 15 illustrates a block diagram illustrating a configuration of the modification example of the ultrasound system of the second embodiment. The ultrasound system illustrated in FIG. 15 is the same as the ultrasound system illustrated in FIG. 8 except that the image information data generation unit 19 of the ultrasound probe 1 includes only the signal processing unit 16 and the information terminal 3 further includes the image processing unit 17, and is the same as the ultrasound system illustrated in FIG. 6 except that the information terminal 3 further includes the terminal-side cine-memory 23.

That is, in the ultrasound system illustrated in FIG. 15, the configurations and operations other than the terminal-side cine-memory 23 are the same as those in the ultrasound system illustrated in FIG. 6.

The terminal-side cine-memory 23 has the same configuration as the terminal-side cine-memory 23 illustrated in FIG. 8, and is operated in the same manner as the terminal-side cine-memory 23 illustrated in FIG. 8, but the terminal-side cine-memory 23 illustrated in FIG. 15 stores, as the image information data, the image signal data instead of the ultrasound image in the case of the live mode.

Next, the operation of the ultrasound system illustrated in FIG. 15 will be described.

In the case of the live mode, except for the terminal-side cine-memory 23, the ultrasound system is operated in the same manner as the ultrasound system illustrated in FIG. 6.

The terminal-side cine-memory 23 is operated in the same manner as the terminal-side cine-memory 23 illustrated in FIG. 8 except that the terminal-side cine-memory 23 stores, as the image information data, the image signal data instead of the ultrasound image.

In the ultrasound system illustrated in FIG. 15, instead of bidirectionally connecting the terminal-side cine-memory 23 to the terminal-side wireless communication circuit 32, the terminal-side cine-memory 23 may be bidirectionally connected to the image processing unit 17, and the terminal-side cine-memory 23 may store the ultrasound image generated by the image processing unit 17 instead of the image signal data. In this case, the terminal-side cine-memory 23 and the display control unit 33 are operated in the same manner as the terminal-side cine-memory 23 and the display control unit 33 illustrated in FIG. 8.

The ultrasound probe 1 according to each embodiment described above can constitute an ultrasound system in combination with the information terminal 3 in which a touch sensor is combined with the monitor 34 and the touch sensor is used as the input device 37. Such an ultrasound system is extremely effective for outdoor diagnosis in a case of emergency treatment and the like.

In the device of the present invention, the hardware configurations of the processing units executing various kinds of processing such as the transmission and reception circuit 14, the image information data generation unit 19, the signal processing unit 16, the image processing unit 17, the frame adjustment unit 15, the probe control unit 21, the error generation unit 26, the display control unit 33, the terminal control unit 36, and the input device 37 may be dedicated hardware, or may be various processors or computers that execute programs. The hardware configuration of the probe-side cine-memory 22 and the terminal-side cine-memory 23 may be dedicated hardware, or may be a memory such as a semiconductor memory. The semiconductor memory constituting the probe-side cine-memory 22 may be provided on a semiconductor of a signal processing processor.

The various processors include a central processing unit (CPU) as a general-purpose processor executing software (program) and functioning as various processing units, a programmable logic device (PLD) as a processor of which the circuit configuration can be changed after manufacturing such as a field programmable gate array (FPGA), and a dedicated electric circuit as a processor having a circuit configuration designed exclusively for executing a specific process such as an application specific integrated circuit (ASIC).

One processing unit may be configured by one of the various processors or may be configured by a combination of the same or different kinds of two or more processors, for example, a combination of a plurality of FPGAs or a combination of an FPGA and a CPU). Further, a plurality of processing units may be configured by one of various processors, or two or more of a plurality of processing units may be collectively configured by using one processor.

For example, there is a form where one processor is configured by a combination of one or more CPUs and software as typified by a computer, such as a server and a client, and this processor functions as a plurality of processing units. Further, there is a form where a processor fulfilling the functions of the entire system including a plurality of processing units by one integrated circuit (IC) chip as typified by a system on chip (SoC) or the like is used.

Furthermore, the hardware configurations of these various processors are more specifically electric circuitry where circuit elements, such as semiconductor elements, are combined.

The method of the present invention can be carried out, for example, by a program for causing a computer to execute each step of the method. Further, a computer-readable recording medium in which this program is recorded can also be provided.

The present invention has been described in detail, but the present invention is not limited to the above-described embodiments, and various improvements and changes may be made within a range not departing from the scope of the present invention.

EXPLANATION OF REFERENCES

1: ultrasound probe
3: information terminal

11: transducer array
14: transmission and reception circuit
15: frame adjustment unit
16: signal processing unit
17: image processing unit
18: probe-side wireless communication circuit
19: image information data generation unit
21: probe control unit
22: probe-side cine-memory
23: terminal-side cine-memory
24: battery
25: probe-side processor
26: error generation unit
32: terminal-side wireless communication circuit
33: display control unit
34: monitor
36: terminal control unit
37: input device
39: terminal-side processor
51: pulser
52: amplification unit
53: AD conversion unit
54: beam former

What is claimed is:

1. An ultrasound system in which an ultrasound probe and an information terminal are wirelessly connected,
wherein the ultrasound probe includes
a transducer array,
a probe-side processor that causes the transducer array to transmit an ultrasonic wave, performs reception focusing processing on a reception signal output from the transducer array that has received an ultrasound echo to generate a sound ray signal, and generates image information data on the basis of the sound ray signal generated,
a probe-side cine-memory that stores the image information data generated by the probe-side processor, and
a probe-side wireless communication circuit that wirelessly transmits the image information data generated by the probe-side processor,
the information terminal includes
a monitor,
an input device,
a terminal-side wireless communication circuit that receives the image information data wirelessly transmitted from the probe-side wireless communication circuit, and
a terminal-side processor that displays an ultrasound image on the monitor on the basis of the image information data received by the terminal-side wireless communication circuit, and
in a case where a freeze mode is designated on the basis of an instruction input from the input device and transmission of the ultrasonic wave from the transducer array is stopped, the image information data of past frames stored in the probe-side cine-memory is wirelessly transmitted from the probe-side wireless communication circuit, and the terminal-side processor displays the ultrasound image on the monitor on the basis of the image information data of the past frames wirelessly transmitted from the probe-side wireless communication circuit after transmission of the ultrasonic wave from the transducer array is stopped and received by the terminal-side wireless communication circuit.

2. The ultrasound system according to claim 1,
wherein the probe-side processor further adjusts whether to output the image information data of all the frames generated or to output the image information data generated by omitting the image information data of at least a part of the frames, according to fluctuations in a wireless transmission band by the probe-side wireless communication circuit, and
in a case where a live mode is designated on the basis of the instruction input from the input device and transmission of the ultrasonic wave from the transducer array is started, the image information data adjusted by the probe-side processor is wirelessly transmitted from the probe-side wireless communication circuit, and the terminal-side processor displays the ultrasound image on the monitor on the basis of the image information data received by the terminal-side wireless communication circuit.

3. The ultrasound system according to claim 2,
wherein the information terminal further includes a terminal-side cine-memory that stores the image information data received by the terminal-side wireless communication circuit,
in the case of the live mode, the image information data adjusted by the probe-side processor is wirelessly transmitted from the probe-side wireless communication circuit, and the image information data received by the terminal-side wireless communication circuit is stored in the terminal-side cine-memory, and
in the case of the freeze mode, the image information data of the at least a part of frames omitted by the probe-side processor is read from the probe-side cine-memory, and is wirelessly transmitted from the probe-side wireless communication circuit, the image information data of the at least a part of frames received by the terminal-side wireless communication circuit is stored in the terminal-side cine-memory, and the terminal-side processor displays the ultrasound image on the monitor on the basis of the image information data stored in the terminal-side cine-memory.

4. The ultrasound system according to claim 3,
wherein immediately after the freeze mode is designated, the image information data of the at least a part of frames omitted by the probe-side processor is wirelessly transmitted from the probe-side wireless communication circuit.

5. The ultrasound system according to claim 3,
wherein on the basis of the instruction input from the input device, the ultrasound image of a frame in the vicinity of the at least a part of frames of the image information data omitted by the probe-side processor is designated from the image information data stored in the terminal-side cine-memory, and immediately after the ultrasound image is displayed on the monitor on the basis of the designated image information data of the frame in the vicinity of the omitted at least a part of frames, the image information data of the at least a part of frames omitted by the probe-side processor is wirelessly transmitted from the probe-side wireless communication circuit.

6. The ultrasound system according to claim 3,
wherein in the case of the freeze mode, the at least a part of frames of the image information data omitted by the probe-side processor is detected from the image information data stored in the terminal-side cine-memory, and the image information data of the at least a part of frames omitted by the probe-side processor is wirelessly transmitted from the probe-side wireless communication circuit on the basis of the detected at least a part of frames of the image information data.

7. The ultrasound system according to claim 6,
wherein detection of the at least a part of frames of the image information data omitted by the probe-side processor is sequentially performed for the frame of the image information data pointed to by a scan pointer, from the frame of the image information data corresponding to the ultrasound image being displayed on the monitor toward the past frame of the image information data among the image information data stored in the terminal-side cine-memory.

8. The ultrasound system according to claim 7,
wherein in a case where the frame of the image information data pointed to by the scan pointer is moved to the past frame of the image information data earlier than the frame of the ultrasound image being displayed on the monitor on the basis of the instruction input from the input device, the frame of the image information data pointed to by the scan pointer is changed to the moved past frame of the image information data, and the detection of the at least a part of frames of the image information data omitted by the probe-side processor is sequentially performed for the frame of the image information data pointed to by the scan pointer, from the changed past frame of the image information data pointed to by the scan pointer toward the latest frame of the image information data, and
in a case where the frame of the image information data pointed to by the scan pointer reaches the latest frame of the image information data, the frame of the image information data pointed to by the scan pointer is changed to the moved past frame of the image information data, and the detection of the at least a part of frames of the image information data omitted by the probe-side processor is sequentially performed for the frame of the image information data pointed to by the scan pointer, from the changed past frame of the image information data pointed to by the scan pointer toward the past frame of the image information data which is further earlier than the changed past frame of the image information data.

9. The ultrasound system according to claim 3,
wherein in the case of the live mode, the probe-side processor generates an omitted frame list for managing the at least a part of frames of the image information data omitted from the image information data wirelessly transmitted by the probe-side wireless communication circuit, and
in the case of the freeze mode, the image information data of the at least a part of frames omitted by the probe-side processor is wirelessly transmitted from the probe-side wireless communication circuit on the basis of the omitted frame list generated by the probe-side processor.

10. The ultrasound system according to claim 3,
wherein the number of frames of the image information data to be stored in the probe-side cine-memory and the number of frames of the image information data to be stored in the terminal-side cine-memory are matched by deciding the number of frames of the image information data to be stored in one of the probe-side cine-memory and the terminal-side cine-memory, which has a larger memory capacity, in accordance with one of the probe-side cine-memory and the terminal-side cine-memory, which has a smaller memory capacity.

11. The ultrasound system according to claim 3,
wherein in the case of the live mode, the image information data of all the frames generated by the probe-side processor is stored in the probe-side cine-memory, and
in the case of the freeze mode, the image information data of the frame wirelessly transmitted from the probe-side wireless communication circuit and the image information data of the frame for which reception confirmation is notified from the information terminal are deleted from the probe-side cine-memory.

12. The ultrasound system according to claim 11,
wherein in the case of the live mode, the image information data of the frame deleted from the terminal-side cine-memory is deleted from the probe-side cine-memory.

13. The ultrasound system according to claim 11,
wherein the probe-side cine-memory generates a free space management list for managing a free space of the probe-side cine-memory in the case of the freeze mode,
in the case of the freeze mode, a frame region of the probe-side cine-memory where the image information data of the frame deleted from the probe-side cine-memory is stored is the free space in the free space management list, and
in the case of the live mode, the image information data of each frame generated by the probe-side processor is sequentially stored from the frame region of the probe-side cine-memory corresponding to a head free space of the free space management list.

14. The ultrasound system according to claim 3,
wherein in the case of the live mode, only the image information data of the at least a part of frames omitted by the probe-side processor is stored in the probe-side cine-memory, and
in the case of the freeze mode, the image information data of the frame for which reception confirmation is notified from the information terminal is deleted from the probe-side cine-memory.

15. The ultrasound system according to claim 14,
wherein the probe-side processor further issues an error when the probe-side cine-memory becomes full in the case of the live mode.

16. The ultrasound system according to claim 3,
wherein the probe-side processor generates image signal data before imaging into the ultrasound image on the basis of the sound ray signal generated, and generates the ultrasound image as the image information data on the basis of the image signal data generated, and
the terminal-side processor displays the ultrasound image received by the terminal-side wireless communication circuit on the monitor.

17. The ultrasound system according to claim 3,
wherein the probe-side processor generates image signal data before imaging into the ultrasound image as the image information data on the basis of the sound ray signal generated,
the terminal-side processor further generates the ultrasound image on the basis of the image signal data received by the terminal-side wireless communication circuit, and displays the ultrasound image generated on the monitor.

18. The ultrasound system according to claim 17,
wherein the terminal-side cine-memory stores the ultrasound image generated by the terminal-side processor.

19. A control method of an ultrasound system in which an ultrasound probe and an information terminal are wirelessly connected, the control method comprising:
- a step of causing a transducer array to transmit an ultrasonic wave, and performing reception focusing processing on a reception signal output from the transducer array that has received an ultrasound echo to generate a sound ray signal, by a probe-side processor of the ultrasound probe;
- a step of generating image information data on the basis of the generated sound ray signal, by the probe-side processor of the ultrasound probe;
- a step of storing the generated image information data, by a probe-side cine-memory of the ultrasound probe;
- a step of wirelessly transmitting the generated image information data, by a probe-side wireless communication circuit of the ultrasound probe;
- a step of receiving the wirelessly transmitted image information data, by a terminal-side wireless communication circuit of the information terminal; and
- a step of displaying an ultrasound image on a monitor on the basis of the received image information data, by a terminal-side processor of the information terminal,
- wherein in a case where a freeze mode is designated on the basis of an instruction input from an input device and transmission of the ultrasonic wave from the transducer array is stopped, the image information data of past frames stored in the probe-side cine-memory is wirelessly transmitted from the probe-side wireless communication circuit, and the terminal-side processor displays the ultrasound image on the monitor on the basis of the image information data of the past frames wirelessly transmitted from the probe-side wireless communication circuit after transmission of the ultrasonic wave from the transducer array is stopped and received by the terminal-side wireless communication circuit.

20. The control method of an ultrasound system according to claim 19, further comprising:
- a step of adjusting whether to output the image information data of all the frames generated or to output the image information data generated by omitting the image information data of at least a part of the frames, according to fluctuations in a wireless transmission band by the probe-side wireless communication circuit, by the probe-side processor of the ultrasound probe,
- wherein in a case where a live mode is designated on the basis of the instruction input from the input device and transmission of the ultrasonic wave from the transducer array is started, the image information data adjusted by the probe-side processor is wirelessly transmitted from the probe-side wireless communication circuit, and the terminal-side processor displays the ultrasound image on the monitor on the basis of the image information data received by the terminal-side wireless communication circuit.

21. The control method of an ultrasound system according to claim 20, further comprising:
- a step of storing the image information data received by the terminal-side wireless communication circuit, by a terminal-side cine-memory of the information terminal,
- wherein in the case of the live mode, the image information data adjusted by the probe-side processor is wirelessly transmitted from the probe-side wireless communication circuit, and the image information data received by the terminal-side wireless communication circuit is stored in the terminal-side cine-memory, and
- in the case of the freeze mode, the image information data of the at least a part of frames omitted by the probe-side processor is read from the probe-side cine-memory, and is wirelessly transmitted from the probe-side wireless communication circuit, the image information data of the at least a part of frames received by the terminal-side wireless communication circuit is stored in the terminal-side cine-memory, and the terminal-side processor displays the ultrasound image on the monitor on the basis of the image information data stored in the terminal-side cine-memory.

22. The control method of an ultrasound system according to claim 21,
- wherein in the case of the live mode, the image information data of all the frames generated by the probe-side processor is stored in the probe-side cine-memory, and
- in the case of the freeze mode, the image information data of the frame wirelessly transmitted from the probe-side wireless communication circuit and the image information data of the frame for which reception confirmation is notified from the information terminal are deleted from the probe-side cine-memory.

23. The control method of an ultrasound system according to claim 21,
- wherein in the case of the live mode, only the image information data of the at least a part of frames omitted by the probe-side processor is stored in the probe-side cine-memory, and
- in the case of the freeze mode, the image information data of the frame for which reception confirmation is notified from the information terminal is deleted from the probe-side cine-memory.

* * * * *